United States Patent
Oshaish et al.

(10) Patent No.: US 12,276,652 B1
(45) Date of Patent: Apr. 15, 2025

(54) DETECTION OF WATER IN OIL EMULSIONS USING SPECTRAL INDUCED POLARIZATION

(71) Applicant: KING FAHD UNIVERSITY OF PETROLEUM AND MINERALS, Dhahran (SA)

(72) Inventors: Ali Abdulwahab Oshaish, Dhahran (SA); Mohamed Mahmoud, Dhahran (SA); Panteleimon Soupios, Dhahran (SA); Ammar El-Husseiny, Dhahran (SA); Panagiotis Kirmizakis, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 18/760,215

(22) Filed: Jul. 1, 2024

Related U.S. Application Data

(60) Provisional application No. 63/553,671, filed on Feb. 15, 2024.

(51) Int. Cl.
*G01N 33/28* (2006.01)
*G01N 15/02* (2024.01)
(Continued)

(52) U.S. Cl.
CPC ..... *G01N 33/2847* (2013.01); *G01N 15/0205* (2013.01); *G01N 15/0266* (2013.01);
(Continued)

(58) Field of Classification Search
CPC .......... G01N 33/2847; G01N 15/0205; G01N 15/0266; G01N 33/2823; G01N 2015/003; G01V 3/06
(Continued)

(56) References Cited

U.S. PATENT DOCUMENTS

| 11,709,141 B2 * | 7/2023 | Alvarez | G01N 33/2847 342/22 |
| 11,933,119 B1 * | 3/2024 | Abdulrazzaq | E21B 21/062 |

(Continued)

FOREIGN PATENT DOCUMENTS

IN 202211072354 A 12/2022

OTHER PUBLICATIONS

Gamal Z. Abdel Aal, et al., "Spectral induced polarization (SIP) response of biodegraded oil in porous media", Geophysical Journal International, vol. 196, No. 2, Nov. 28, 2013, pp. 804-817.
(Continued)

*Primary Examiner* — Raul J Rios Russo
*Assistant Examiner* — Trung Q Nguyen
(74) *Attorney, Agent, or Firm* — Oblon, McClelland, Maier & Neustadt, L.L.P.

(57) ABSTRACT

A method of emulsion detection includes executing an oil production process from a volume of a formation. While executing the oil production process, conducting real-time spectral induced polarization (SIP) measurements of the volume of the formation to determine a real-time real conductivity value (RCV) of a matrix material in the volume of the formation. The method further includes determining an onset of water-in-oil (W/O) emulsion formation in the volume of the formation by analyzing the real-time RCV of the matrix material and optionally identifying the onset of the W/O emulsion formation when the real-time RCV first exceeds a first threshold value.

16 Claims, 17 Drawing Sheets

(51) Int. Cl.
 *G01N 15/0205* (2024.01)
 *G01V 3/06* (2006.01)
 *G01N 15/00* (2006.01)

(52) U.S. Cl.
 CPC ........... *G01N 33/2823* (2013.01); *G01V 3/06* (2013.01); *G01N 2015/003* (2013.01)

(58) Field of Classification Search
 USPC ............................... 324/500, 600, 76.11, 96
 See application file for complete search history.

(56) References Cited

U.S. PATENT DOCUMENTS

| | | | | |
|---|---|---|---|---|
| 2007/0189452 | A1* | 8/2007 | Johnson | G01F 1/86 378/53 |
| 2010/0042335 | A1* | 2/2010 | Murphy | G01N 33/2823 702/30 |
| 2015/0168368 | A1* | 6/2015 | Hegazi | G01N 33/2847 73/61.48 |
| 2016/0291194 | A1 | 10/2016 | Marsala et al. | |
| 2016/0333686 | A1* | 11/2016 | Scott | E21B 49/08 |
| 2017/0073571 | A1* | 3/2017 | Salla | E21B 37/06 |
| 2020/0072776 | A1* | 3/2020 | Børresen | G01N 13/00 |
| 2022/0258074 | A1* | 8/2022 | Meribout | B01D 19/0063 |

OTHER PUBLICATIONS

Thomas Kremer, et al., "Modelling the spectral induced polarization response of water-saturated sands in the intermediate frequency range ( 102-105 Hz) using mechanistic and empirical approaches", Geophysical Journal International, 2016, pp. 1303-1312.

Sara Kellal, et al., "Innovative application of spectral induced polarization (SIP) for oil detection in low resistivity pay zones", Dec. 13, 2023, 2 pages.

* cited by examiner

DETECTION OF WATER IN OIL EMULSIONS USING SPECTRAL INDUCED POLARIZATION

CROSS REFERENCE TO RELATED APPLICATIONS

Aspects of the present disclosure are related to Applicant's co-pending patent application Ser. No. 18/528,048 filed on Dec. 4, 2023, titled "DETECTION OF LOW RESISTIVITY PAY ZONES USING SPECTRAL INDUCED POLARIZATION METHOD", which is incorporated herein by reference in its entirety. This present disclosure claims the benefit of U.S. Provisional Application No. 63/553,671, filed on Feb. 15, 2024, which is incorporated herein by reference in its entirety.

BACKGROUND

Technical Field

The present disclosure is directed to the field of petroleum production, and more specifically to a method for detecting and monitoring formation of water-in-oil (W/O) emulsions during oil extraction processes using spectral induced polarization (SIP) measurements.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The extraction and processing of petroleum from subterranean formations have long been accompanied by various challenges related to the management and separation of extracted fluids. With the continuous exploitation of oil reserves, water production becomes inevitable, which is the main reason for multiphase flow and the formation of different types of emulsions [See: Abed, S. M., Abdurahman, N. H., Yunus, R. M., Abdulbari, H. A., & Akbari, S. (2019 November)—*Oil emulsions and the different recent demulsification techniques in the petroleum industry—A review*, In IOP Conference Series: Materials Science and Engineering (Vol. 702, No. 1, p. 012060), IOP Publishing; Sousa, A. M., Pereira, M. J., & Matos, H. A. (2022)—*Oil-in-water and water-in-oil emulsions formation and demulsification, Journal of Petroleum Science and Engineering*, 210, 110041]. Emulsions can be formed in any part of the flow path, including the porous rocks [See: Gómora-Figueroa, A. P., Camacho-Velázquez, R. G., Guadarrama-Cetina, J., & Guerrero-Sarabia, T. I. (2019)—*Oil emulsions in naturally fractured Porous Media. Petroleum*, 5 (3), 215-226] and the downstream pipelines [See: Hart, A. (2014)—*A review of technologies for transporting heavy crude oil and bitumen via pipelines, Journal of Petroleum Exploration and Production Technology*, 4, 327-336; Sousa et al., 2022; and Fatemeh Goodarzi, Sohrab Zendehboudi (2019)—*A Comprehensive Review on Emulsions and Emulsion Stability in Chemical and Energy Industries, The Canadian Journal of Chemical Engineering*, Volume 97, Issue 1].

Although there are various types of oil-water emulsions which can form depending on which fluid is the continuous phase [See: Abdulredha, M. M., Aslina, H. S., & Luqman, C. A. (2020)—*Overview on petroleum emulsions, formation, influence and demulsification treatment techniques, Arabian Journal of Chemistry*, 13 (1), 3403-3428], water-in-oil (W/O) emulsion is the most common type occurring at an early stage of production [See: Kokal, S. (2005)—*Crude-oil emulsions: A state-of-the-art review, SPE Production & facilities*, 20 (01), 5-13]. The W/O emulsion can be described as emulsions where the oil forms the continuous phase and the water forms isolated droplets. These emulsions could result in undesirable consequences inside the reservoir and through the downstream, such as limiting the relative mobility of the oil inside the reservoir and causing high-pressure declines in the flowlines, as well as other pressure and operational problems in the separators and surface facilities. These problems do not only reduce the efficiency of oil recovery but also increase the costs associated with treatment and disposal of emulsions. Therefore, it is necessary to detect water encroachment in time and implement the required mitigation and prevention measures to either stop or reduce it.

The W/O emulsions can vary significantly in their composition and stability depending on the specific conditions of the reservoir and the fluids involved. Specifically, water concentration can range from 0-70% while the droplet size varies widely (between 0.4 µm and 100 µm) depending on the emulsifying solids and the emulsification mechanism [See: Shah, A.; Fishwick, R.; Wood, J.; Leeke, G.; Rigby, S.; Greaves, M.—*A review of novel techniques for heavy oil and bitumen extraction and upgrading. Energy Environ, Sci.* 2010, 3, 700-714; Maia Filho, D. C.; Ramalho, J. B.; Spinelli, L. S.; Lucas, E. F.—*Aging of water-in-crude oil emulsions: Effect on water content, droplet size distribution, dynamic viscosity and stability, Colloids Surf. A Physicochem. Eng. Asp.* 2012, 396, 208-212; Morgan, V. G.; Sad, C.; Constantino, A. F.; Azeredo, R. B.; Lacerda, V.; Castro, E. V.; Barbosa, L. L.—*Droplet size distribution in water-crude oil emulsions by low-field NMR, J. Braz. Chem. Soc.* 2019, 30, 1587-1598; and Silva, C. A.; Saraiva, S. V.; Bonetti, D.; Higuti, R. T.; Cunha, R. L.; Pereira, L. O.; Silva, F. V.; Fileti, A. M.—*Application of acoustic models for polydisperse emulsion characterization using ultrasonic spectroscopy in the long wavelength regime, Colloids Surf. A Physicochem. Eng. Asp.* 2020, 602, 125062]. The droplet size is one factor that highly affects the stability of the emulsion and controls its type, and also has a significant impact on different measurement techniques which are utilized for emulsions. Therefore, it may be important to consider the droplet size while studying the response of different measurements to analyze emulsions.

Several techniques are available to monitor and characterize emulsions, such as light and electron microscopy, neutron scattering, Nuclear Magnetic Resonance (NMR) [See: Raigan, K.—*Ultrasonic Techniques for Characterizations of Oils and Their Emulsions and Monitoring Oil Layer Depth of Spill Emulsions and Monitoring Oil Layer Depth of Spill*, Ph.D. Thesis, The University of Western Ontario, London, ON, Canada, 2020; Morgan et al., 2019], centrifugation [See: Jadoon, S.; Malik, A.; Amin, A. A. *Separation of Sediment Contents and Water from Crude Oil of Khurmala and Guwayer Oil Fields in Kurdistan Region by using Centrifuge Method. Int. J. Adv. Eng. Res. Sci.* 2017, 4, 2919-2922], grinding methods and Karl and Fisher's distillation [See: Ivanova, P. G.; Aneva, Z. V. *Assessment and assurance of quality in water measurement by coulometric Karl Fischer titration of petroleum products. Accredit. Qual. Assur.* 2006, 10, 543-549]. However, most of these techniques have measurement limitations when they are used with water in oil emulsions, restricted to diluted and non-opaque oil in water emulsions. For example, light, electron and neutron-based measurements are suitable for non-opaque water diluted conditions which cannot be exhibited by W/O emulsions. Other techniques such as grinding, distillation and centrifuge require fluid sampling which takes time, hinders real-time measurements and does not allow early detections.

US 2016/0291194A1 describes a method of detecting an area having more hydrocarbons when a subterranean zone has a non-uniform distribution of hydrocarbons. Two areas can be measured by induced polarization. The difference in phase and amplitude between the two areas can be recorded and stored for each frequency. However, this reference does not disclose the use of real-time spectral induced polarization (SIP) measurements for determining an onset of water-in-oil (W/O) emulsion formation in a volume of a formation, as required for purposes of the present disclosure. IN Patent Reference No. 202211072354A describes the use of spectral induced polarization (SIP) to determine pore size distribution using the double Cole-Cole method. While it involves the measurement of real and imaginary parts of the conductivity at different frequencies, it is a different technique for solving a different problem as compared to the present disclosure. The effect of different oil saturation (0.2-0.8) and wetting conditions (water-wet and oil-wet) on the spectral induced polarization (SIP) response of oil in sand columns has been studied [See: Gamal Z. Abdel Aal, Estella A. Atekwana—*Spectral induced polarization (SIP) response of biodegraded oil in porous media, Geophysical Journal International*, Volume 196, Issue 2, February 2014, Pages 804-817]. When oil is the wetting phase, the real conductivity monotonically decreases with oil saturation in FIG. 7C. This reference fails to recognize the non-monotonical relationship around the onset of oil-water emulsion formation, which can be used to detect the onset of emulsion in the present disclosure.

Each of the aforementioned references suffers from one or more drawbacks hindering their adoption. Most notable is their inability to provide real-time data and continuous monitoring without disrupting production. These limitations hinder effective decision-making and timely intervention, often resulting in increased operational costs and potential environmental impacts. Accordingly, it is one object of the present disclosure to provide a method of emulsion detection that can detect the formation of water-in-oil emulsions in real-time during the oil production process.

SUMMARY

In an exemplary embodiment, a method of emulsion detection is described. The method comprises executing an oil production process from a volume of a formation. The method further comprises, while executing the oil production process, conducting real-time spectral induced polarization (SIP) measurements of the volume of the formation to determine a real-time real conductivity value (RCV) of a matrix material in the volume of the formation. The method further comprises determining an onset of water-in-oil (W/O) emulsion formation in the volume of the formation by analyzing the real-time RCV of the matrix material. The method further comprises identifying the onset of the W/O emulsion formation when the real-time RCV first exceeds a first threshold value.

In some embodiments, the method further comprises, before executing the oil production process, conducting an initial SIP measurement of the volume of the formation to determine an initial RCV of the matrix material.

In some embodiments, the first threshold value is at least 100 times the initial RCV.

In some embodiments, the first threshold value is at least 1000 times the initial RCV.

In some embodiments, the onset of the W/O emulsion formation is identified when the real-time RCV first becomes at least 100 times of the initial RCV before reaching a maximum value and then decreasing.

In some embodiments, the method further comprises, while executing the oil production process, conducting real-time laser measurements of the volume of the formation to determine a real-time particle size value of the matrix material. The method further comprises confirming the onset of the W/O emulsion formation when the real-time particle size value exceeds a second threshold value.

In some embodiments, before executing the oil production process, the method further comprises obtaining a plurality of samples containing water and the matrix material with water percentage ranging from 0 vol. % to 100 vol. %. The method further comprises conducting a plurality of SIP measurements of the plurality of samples to determine a plurality of RCVs. The method further comprises determining the first threshold value based on the plurality of RCVs.

In some embodiments, the method further comprises conducting a plurality of laser measurements of the plurality of samples to determine a plurality of particle sizes. The method further comprises determining the second threshold value by comparing the plurality of RCVs and the plurality of particle sizes.

In some embodiments, the method further comprises plotting the plurality of RCVs against the water percentage of the plurality of samples. The method further comprises determining a critical water concentration for the onset of the W/O emulsion formation.

In some embodiments, the method further comprises determining a range of water percentage for the W/O emulsion formation.

In some embodiments, the initial SIP measurement and the real-time SIP measurements are performed at a frequency of 0.1 Hz or more, and 100 Hz or less.

In some embodiments, the initial SIP measurement and the real-time SIP measurements are performed at a single frequency or a plurality of individual frequencies.

In some embodiments, the initial SIP measurement and the real-time SIP measurements are performed at at least one frequency selected from the group consisting of 0.1 Hz, 1 Hz, 10 Hz or 100 Hz.

In some embodiments, the initial SIP measurement and the real-time SIP measurements do not include frequency sweeps over a frequency range.

In some embodiments, the method further comprises obtaining the real-time SIP measurements of the volume of the formation using an SIP device. The SIP device comprises an SIP column including a plurality of potential electrodes arranged along a longitudinal direction of the SIP column. The SIP device further comprises two current electrodes positioned on opposing ends of the SIP column.

In some embodiments, obtaining the SIP measurements comprises obtaining a first set of SIP measurements between two potential electrodes of the plurality of potential electrodes, and obtaining a second set of SIP measurements between another two potential electrodes of the plurality of potential electrodes.

In some embodiments, the method further comprises placing potential electrodes and current electrodes adjacent to the volume of the formation. The method further comprises injecting an alternating electrical current into the formation through the current electrodes. The method further comprises measuring a set of data via the potential electrodes.

In some embodiments, the potential electrodes and the current electrodes are placed at intervals along a borehole adjacent to the volume of the formation or on a ground surface above the volume of the formation.

In some embodiments, injecting the alternating electrical current and measuring the set of data are executed simultaneously.

In some embodiments, the set of data include the real-time RCV and at least one selected from the group consisting of an imaginary conductivity, a phase shift and an impedance distribution.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
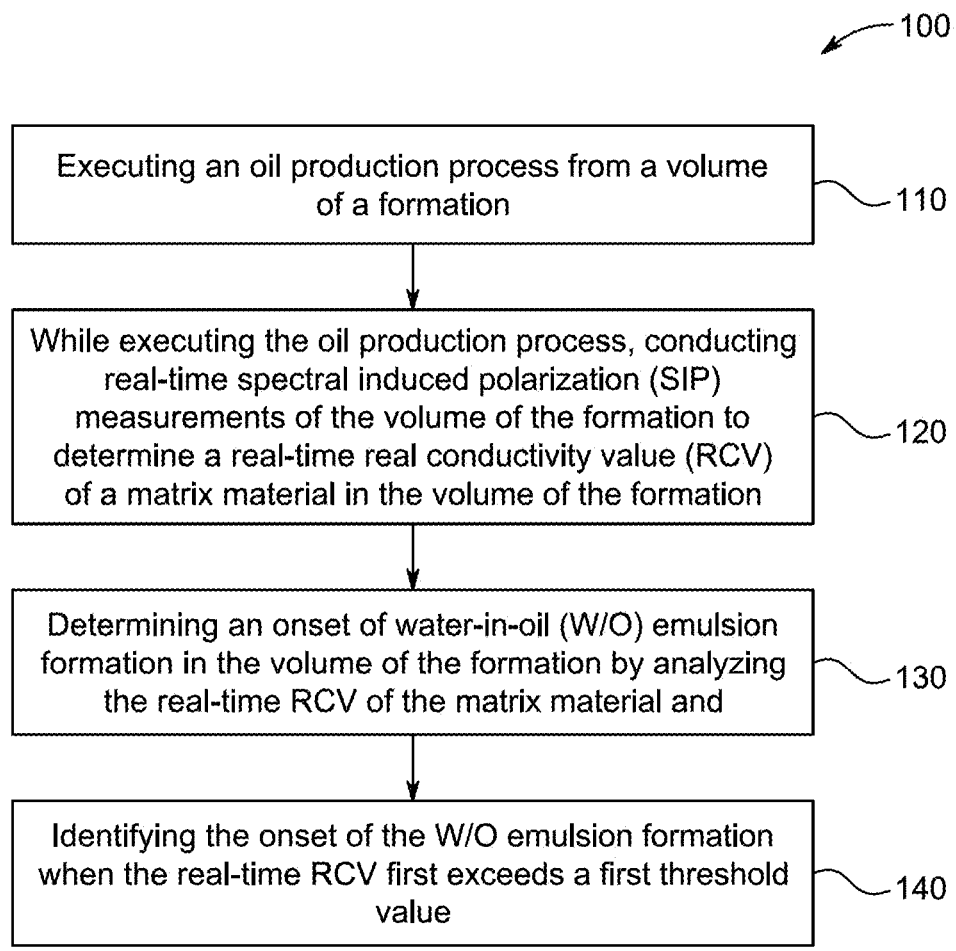
FIG. 1 is an exemplary flowchart of a method of emulsion detection, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

In recent decades, geophysical exploration has made substantial use of electric logging and surveying instruments. For lithological identification, pay zone detection, and the detection of any disturbances in the petroleum and rock system surrounding the reservoir and wellbore, techniques like self-potential logging (SP), resistivity logging, induced polarization (IP) surveying, and many others have been used [See: Heenan, J., Porter, A., Ntarlagiannis, D., Young, L. Y., Werkema, D. D., & Slater, L. D. (2013)—*Sensitivity of the spectral induced polarization method to microbial enhanced oil recovery processes, Geophysics*, 78 (5); Ntarlagiannis, D., Kirmizakis, P., Kalderis, D., & Soupios, P. (2016)—*Using the spectral induced polarization method to assess biochar performance as a remediation agent, AGU Fall Meeting* 2016, incorporated herein by reference in their entirety]. The IP technique was applied in its infancy for minerals detection in the 1930s, but it was constrained by the early low computation capabilities [See: Rust, W. M. (1938)—*A historical review of electrical prospecting methods, Geophysics*, 3 (1), 1-6]. The IP approach was later employed and modified to be able to be used in the time domain and frequency domain as spectral induced polarization (SIP), after the advent of powerful computing capabilities.

SIP is an electrical geophysical technique where the measurements can be acquired under a wide range of frequencies. SIP is widely used in geophysical monitoring, where it has been used for concentration assessment [See: Izumoto, S., Huisman, J. A., Wu, Y., & Vereecken, H. (2020)—*Effect of solute concentration on the spectral induced polarization response of calcite precipitation. Geophysical Journal International*, 220 (2), 1187-1196; Martin, T. (2014)—*Laboratory SIP-investigation on unconsolidated mineral-sand-mixtures, 3rd International Workshop on Induced Polarization, April*, incorporated herein by reference in their entirety], grain size effect studies [See: Revil, A., Karaoulis, M., Johnson, T., & Kemna, A. (2012)—*Review: Some low-frequency electrical methods for subsurface characterization and monitoring in hydrogeology, Hydrogeology Journal*, 20 (4), 617-658; Revil, A., & Florsch, N. (2010)—*Determination of permeability from spectral induced polarization in granular media, Geophysical Journal International*, 181 (3), 1480-1498, incorporated herein by reference in their entirety], microbial monitoring of iron sulfides [See: Yves Robert Personna, Dimitrios Ntarlagiannis, Lee Slater, Nathan Yee, Michael O'Brien, Susan Hubbard-Spectral induced polarization and electrodic potential monitoring of microbially mediated iron sulfide transformations, Journal of Geophysical Research 2008), incorporated herein by reference in its entirety], and other purposes. The distinct characteristic of this measurement over the traditional electrical measurement arises from its sensitivity to the presence of different compartments with a large variation in their electrical properties. Since oil and water have a high contrast in their electrical conductivities, electrical geophysical methods and especially SIP can be used efficiently to detect and analyze the emulsions droplets.

Aspects of this disclosure are directed to a method of emulsion detection. In particular, the present disclosure provides the method for detecting the formation of water-in-oil emulsions during oil production processes. The method of the present disclosure involves conducting real-time SIP measurements to monitor the real conductivity values of matrix materials within the formation. By analyzing these values against predetermined thresholds, the method can determine and identify the onset of emulsion formation, enabling timely interventions to manage the production process effectively.

Referring to FIG. 1, illustrated is an exemplary flowchart of a method (as represented by reference numeral 100) of emulsion detection. The method 100 provides a systematic approach or procedure designed to identify the presence and onset of emulsions within a specific environment, for instance during the oil production process. The method 100 utilizes techniques to monitor and analyze the properties of the substances involved in the oil production process to detect changes that indicate the formation of emulsions. As used herein, the "emulsion" is a mixture of at least two immiscible liquids where one liquid (e.g., water) is dispersed (e.g., in the form of droplets) within another liquid (e.g., oil). These emulsions are commonly known as water-in-oil (W/O) emulsions. "Detection," in present context, involves identifying the onset or presence of these water-in-oil emulsions in real-time during the oil production process. The ability of the method 100 to detect emulsions effectively allows for timely interventions that can mitigate the potential negative impacts associated with emulsion formation, such as increased operational costs and environmental risks.

At step 110, the method 100 includes executing an oil production process from a volume of a formation. The step 110 refers to an initial stage of the overall process where the extraction of oil is carried out from a specified geological formation. The oil production process can include drilling into a geological formation to access the oil reservoir and the extraction of crude oil from underground reservoir which is part of the geological formation. The "volume of a formation" refers to the specific segment or portion of the geological formation from which the oil is being extracted. Such formation consists of various layers of earth and rock that contain accumulations of hydrocarbons, primarily oil and natural gas. The extraction process involves using various techniques to bring the oil to the surface. These techniques may include natural drive mechanisms such as gas drive, water injection, or artificial lift technologies like pump jacks and downhole pumps. This process also involves the management of the operational flow of the extracted oil, including the handling of the crude oil as it is brought to the surface, along with any accompanying natural gas or water that is co-extracted. An actual IP or SIP setup for measuring a geological formation is known in the art and will thus be omitted here for simplicity purposes. For example, US 2016/0291194A1 discloses a configuration in FIG. 1, which can be used for techniques herein, with known oil production conditions and methods.

At step 120, the method 100 includes, while executing the oil production process, conducting real-time spectral induced polarization (SIP) measurements of the volume of the formation to determine a real-time real conductivity value (RCV) of a matrix material in the volume of the formation. SIP is a geophysical technique used to measure the electrical properties of subsurface materials by inducing an electrical field and analyzing the resultant polarization effects. The key parameters measured by SIP include real and imaginary components of electrical conductivity. These measurements provide insights into physical and chemical properties of the formation, such as porosity, fluid saturation, and the presence of different phases within the fluids. The term "real-time," in present context, means that the SIP measurements are conducted simultaneously with the oil extraction process, providing immediate data on the condition of the formation. This allows for detecting early signs of water breakthrough and the onset of emulsion formation. That is, the real-time aspect of these measurements ensures that data is obtained and analyzed simultaneously with the ongoing oil production operations, allowing for immediate responses to any detected changes.

Further, herein, the RCV refers to the measurement of the real component of electrical conductivity within the matrix material. The matrix material typically includes the rock and other geological substances surrounding the oil. The electrical conductivity within the matrix material is indicative of how easily electric current can pass through the matrix material. It is directly influenced by the presence and characteristics of fluids within the rock pores, such as oil, water, and gas. The process to determine the RCV involves using SIP techniques, where an electric field is induced in the formation and the resultant electrical responses are measured. The real part of the conductivity measurement focuses on the resistive properties of the formation and is particularly sensitive to the saline water content in the formation because saline water is more conductive than oil. As the water content increases, especially when it forms an emulsion with oil, there is a notable change in the RCV. For instance, an increase in the RCV can indicate the onset of water-in-oil emulsion formation. Detecting these changes in real-time allows operators to take preventive or corrective actions to manage the emulsion.

At step 130, the method 100 includes determining an onset of water-in-oil (W/O) emulsion formation in the volume of the formation by analyzing the real-time RCV of the matrix material. This step 130 involves analyzing the conductivity data obtained from the SIP measurements to identify the initial formation of emulsions within the oil production process. As discussed in the preceding paragraphs, the real-time RCV, which reflects the real part of the electrical conductivity of the matrix material, is continuously monitored during the oil production process. The analysis focuses on detecting any significant changes in the RCV that could indicate the presence of water within the oil or the formation of an emulsion. Inventors have found that the real part of the conductivity (i.e., the RCV) is particularly sensitive to the presence of water because water has a higher electrical conductivity compared to oil. An increase in water content within the oil leads to a higher RCV, indicating potential emulsion formation, and accordingly the W/O emulsion formation is detected. The onset of W/O emulsion is significant because water droplets dispersed in oil can alter the physical and chemical properties of the extracted fluid, affecting both the efficiency and the cost of the oil production process. At step 140, the method 100 includes identifying the onset of the W/O emulsion formation when the real-time RCV first exceeds a first threshold value. That is, the onset of the W/O emulsion formation is identified when the RCV reaches or exceeds the first threshold value. The first threshold value for the real-time RCV can be pre-determined based on experimental data and prior observations that relate specific conductivity values with the presence of emulsions. The first threshold value is set to reflect a significant change in conductivity that is consistent with the physical characteristics of water beginning to mix with oil in the formation. By setting the first threshold value, the method 100 provides a quantitative criterion for detecting the initial stages of emulsion formation. Specifically, in the method 100, SIP measurements are continuously conducted to monitor the RCV of the matrix material in real-time. This involves the collection and analysis of electrical conductivity data directly from the formation. Once the RCV exceeds the first threshold value, the event is identified as the onset of the W/O emulsion formation.

Therefore, the present method 100 involves a systematic approach to detecting the formation of the W/O emulsions during the oil production process by conducting real-time SIP measurements to monitor the real-time RCV of the matrix material within the volume of the formation. The method 100 starts with executing the oil extraction process from the designated volume of a geological formation, during which real-time SIP measurements are continuously conducted. The method 100 involves analyzing the real-time RCV to detect if it exceeds the first threshold value, which indicates the onset of the W/O emulsion formation. This detection allows for immediate operational adjustments to manage or mitigate the effects of emulsions, thus maintaining the efficiency and effectiveness of the oil production process. The adjustments may involve corrective actions to address the emulsion issue, which may include adjusting extraction processes, applying chemical treatments, or implementing physical separation techniques. Effective management of emulsions can reduce downtime caused by equipment blockages or failures and decrease the costs associated with additional processing requirements. By managing emulsions effectively, the overall efficiency of the oil recovery process is improved, ensuring a higher yield and quality of the extracted oil.

In some embodiments, the method 100 includes, before executing the oil production process, conducting an initial SIP measurement of the volume of the formation to determine an initial RCV of the matrix material. That is, the method 100 includes conducting the initial SIP measurement of the volume of the formation before the commencement of the oil production process. This establishes a baseline for the real-time RCV of the matrix material. The initial SIP measurement is taken to assess the electrical properties of the matrix material within the formation without the influence of oil production activities, providing the initial RCV against which all subsequent real-time RCV measurements can be compared. Herein, the initial RCV provides a reference point that aids in the interpretation of changes in the electrical properties of the matrix material. This step may also help with accurate calibration of SIP device (as discussed later in more detail), ensuring that the subsequent real-time measurements taken during the oil production are reliable.

Further, by establishing the initial RCV, it is possible to define the first threshold value that is used to detect the onset of emulsion formation. Specifically, the first threshold value is set based on a multiple of the initial RCV of the matrix material obtained from the volume of the formation. In an embodiment, the first threshold value is at least 100 times the initial RCV. This multiple is chosen to ensure that minor fluctuations in conductivity of the matrix material, which may occur due to other variables such as changes in temperature or pressure, do not trigger false positives, thereby maintaining the reliability of emulsion detection. In another embodiment, the first threshold value is at least 1000 times the initial RCV. This higher multiple may be used in environments where conductivity of the matrix material may show greater fluctuations. By setting the first threshold value using this higher multiple, the method 100 ensures that only significant increases in conductivity, which are more clearly indicative of substantial emulsion formation, are considered. In general, the first threshold value can be 100 times, preferably 500 times, preferably 1000 times, preferably 5000 times, preferably 10000 times or any values therebetween, of the initial RCV.

In an embodiment, the onset of the W/O emulsion formation is identified when the real-time RCV first becomes at least 100 times of the initial RCV before reaching a maximum value and then decreasing. This significant increase in the RCV is an indicator of substantial changes within the formation, particularly the accumulation of water in the oil, which affects the conductivity. Specifically, the method 100 provides that this increase in the real-time RCV occurs before it reaches a maximum value and then begins to decrease. The identification of this peak and subsequent decrease suggests that the maximum concentration of conductive elements (likely water) within the oil has been reached and is now decreasing, potentially due to the movement of fluids within the formation or the beginning of management strategies to address the emulsion. Understanding when the RCV peaks and begins to decrease helps in making informed decisions about the oil production process. If the RCV decreases, it may indicate that the emulsion is becoming less stable. Conversely, if the RCV remains high, it may indicate that more aggressive measures may be required. In an alternative embodiment, the onset of the W/O emulsion formation may be identified when the real-time RCV reaches the maximum value.

In the present method 100, the initial SIP measurement and the real-time SIP measurement are performed within a specific frequency range. This frequency range is deliberately chosen to optimize the detection of changes in electrical properties of the formation that are indicative of emulsion formation. The frequency can refer to a frequency of an alternating electrical current. In an embodiment, the initial SIP measurement and the real-time SIP measurements are performed at a frequency of 0.1 Hz or more, and 100 Hz or less. This frequency range is selected based on its effectiveness in the SIP measurements, where lower frequencies are generally sensitive to the presence of saline water, and higher frequencies can provide information about the capacitive behavior of the matrix material. Specifically, herein, the initial SIP measurement and the real-time SIP measurements can be performed at a single frequency or a plurality of individual frequencies. This allows for a degree of flexibility, enabling the method 100 to be tailored according to the specific geophysical characteristics of the formation. For example, using a single frequency measurement can be suitable for consistent formations, whereas multiple frequency measurements can provide additional data points for more complex formations.

Further, in the present method 100, the initial SIP measurement and the real-time SIP measurements are performed at at least one frequency selected from the group consisting of 0.1 Hz, 1 Hz, 10 Hz or 100 Hz. These specific frequencies have been found to be suitable for monitoring the changes in the emulsion composition in different geological scenarios (as discussed later in more detail in reference to experimental study). Each of these frequencies can provide different readings about electrical properties of the formation. Furthermore, in the present method 100, the initial SIP measurement and the real-time SIP measurements may or may not include frequency sweeps over a frequency range. That is, unlike some SIP approaches that measure across a continuous spectrum of frequencies to capture a broad response, the method 100 can instead utilize fixed, discrete frequencies or a set of individual frequencies, or only a single frequency. This approach avoids the complexity that can arise from interpreting broad-spectrum frequency sweep data. By focusing on specific frequencies, the method 100 provides precision in the SIP measurements, facilitating a straightforward analysis that can be directly correlated with the onset of W/O emulsion formation.

In some embodiments, the method 100 further includes, while executing the oil production process, conducting real-time laser measurements of the volume of the formation to determine a real-time particle size value of the matrix material. Herein, the use of laser measurement technology involves directing a laser beam into the formation and analyzing the light scattering caused by particles within the matrix material. The pattern and intensity of the scattered light are indicative of the size distribution of the particles within the formation. Particle size can be an important factor in emulsion stability; larger or more irregular particles can stabilize emulsions, making them more difficult to treat and manage. It may be noted that these measurements are conducted while executing the oil production process, so as to determine the real-time particle size values. In some embodiments, an initial sample can be taken from the volume of the formation for an initial laser measurement when a bore hole is first drilled. Then, when the real-time RCV reaches the first threshold value, the oil production process may be paused, and another sample can be taken for another laser measurement to confirm the onset of W/O formation.

The method 100 also includes confirming the onset of the W/O emulsion formation when the real-time particle size value exceeds a second threshold value. That is, once the real-time laser measurements are taken and particle sizes are determined, the method 100 then involves confirming the onset of the W/O emulsion formation based on these real-time particle size values. Herein, the second threshold value is set based on experimental data and is indicative of a particle size at which water droplets within the oil start forming a stable emulsion. The second threshold value is designed to be sensitive enough to detect significant emulsion formation early, allowing for timely interventions. The inclusion of this process provides a complementary data set that enhances the overall accuracy and reliability of the method 100 of emulsion detection.

In some embodiments, before executing the oil production process, the method 100 further includes obtaining a plurality of samples containing water and the matrix material with water percentage ranging from 0 vol. % to 100 vol. %. This preparatory phase involves obtaining a range of samples that variably mix water and the matrix material. These samples are specifically prepared with water concentrations that vary from 0 volume percent to 100 volume percent. This broad spectrum of samples allows for a comprehensive analysis covering potential field conditions. The method 100 also includes conducting a plurality of SIP measurements of the plurality of samples to determine a plurality of RCVs. That is, following the collection of the samples, the method 100 includes conducting one or more SIP measurements on each sample. These SIP measurements provide insights into how different water concentrations within the matrix material affect the RCVs. By measuring the RCVs across a range of known water concentrations, the method 100 establishes a profile of conductivity responses corresponding to varying levels of water content within the matrix material. The method 100 can then include determining the first threshold value based on the plurality of RCVs. That is, once the SIP measurements are completed and a dataset of RCVs corresponding to different water percentages is compiled, the method 100, then, determines the first threshold value for the real-time RCV. The first threshold value is determined based on analyzing the patterns and trends observed in the RCVs from the plurality of samples. Typically, this involves identifying an RCV that consistently correlates with the initial formation of emulsions or a significant change in the emulsion stability, as indicated by the prepared samples. This approach enables the method 100 to reliably detect when the real-time RCV, measured during oil extraction, exceeds the first threshold value, for identifying the onset of the W/O emulsion formation.

Figure 2:
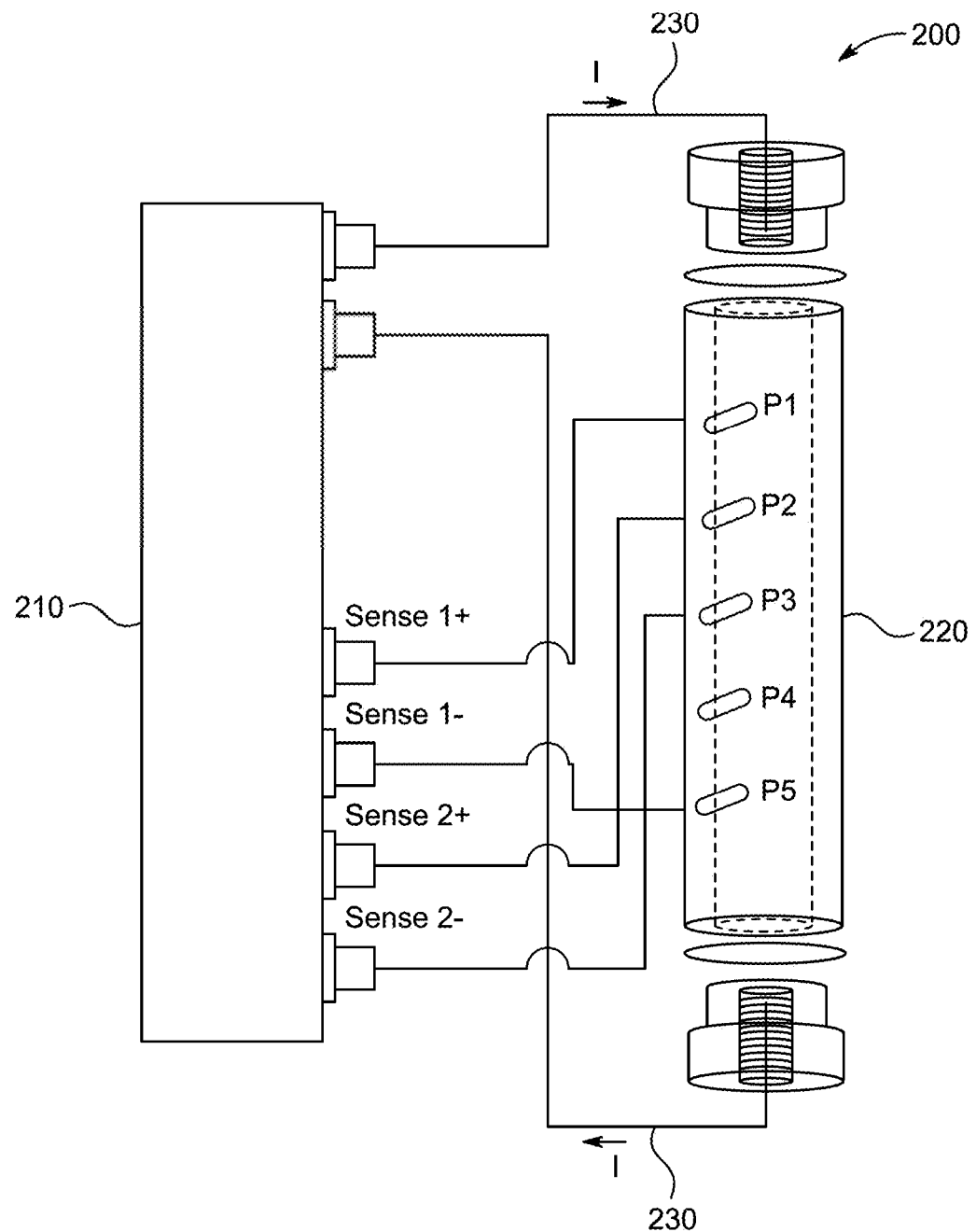
FIG. 2 is a schematic diagram of a spectral induced polarization (SIP) device implemented for emulsion detection, according to certain embodiments.
Figure 3A:
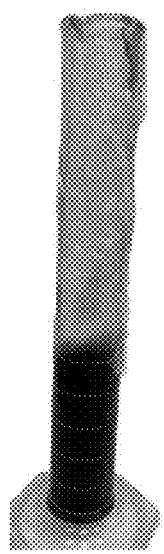
FIG. 3A depicts an emulsion composition for one of the samples used in experimental study, according to certain embodiments.
Figure 3B:
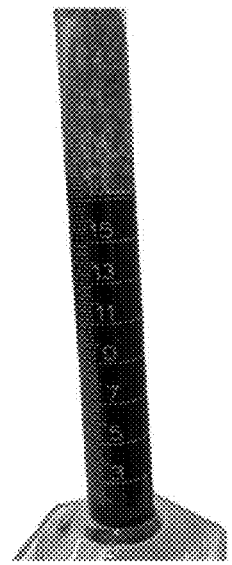
FIG. 3B depicts an emulsion composition for another one of the samples used in experimental study, according to certain embodiments.
Figure 3C:
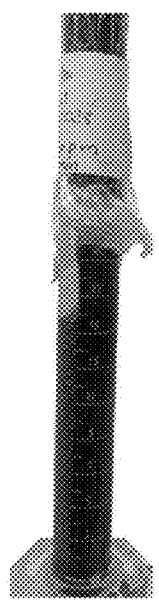
FIG. 3C depicts an emulsion composition for yet another one of the samples used in experimental study, according to certain embodiments.
Figure 3D:
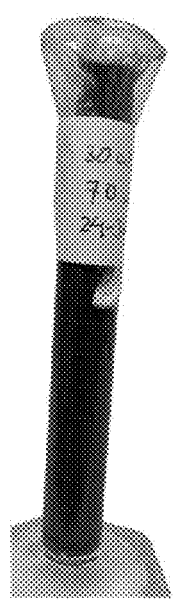
FIG. 3D depicts an emulsion composition for still another one of the samples used in experimental study, according to certain embodiments.

Further, in some embodiments, the method 100 comprises conducting a plurality of laser measurements of the plurality of samples to determine a plurality of particle sizes before executing the oil production process. That is, the method 100 involves conducting a series of laser measurements on the plurality of samples that contain differing concentrations of water mixed with the matrix material, specifically ranging from 0 vol. % to 100 vol. % water content (as discussed in the preceding paragraph), are subjected to laser measurements to determine the particle sizes within each sample. Laser measurement technology, typically involving laser diffraction techniques, is utilized to analyze the light scattered by the particles in the samples, to determine the size distribution of the particles. This provides an understanding of how particle size varies with changes in water content within the matrix material. The method 100, then, includes determining the second threshold value by comparing the plurality of RCVs and the plurality of particle sizes. This comparison helps to identify correlations between specific particle sizes and corresponding RCVs that indicate the formation of emulsions. Specifically, determining the second threshold value involves analyzing the relationship between particle sizes and RCVs to find a particle size value that aligns with significant changes in conductivity indicative of emulsion stability. The second threshold value is then used during the oil production process to monitor real-time particle size measurements. If real-time particle size value exceeds the second threshold value, it suggests the onset of the W/O emulsion formation. Referring now to FIG. 2, illustrated is a schematic of an SIP device (as represented by reference numeral 200), which is utilized for obtaining the real-time SIP measurements of the volume of the formation. As illustrated, the SIP device 200 includes an SIP acquisition unit 210. The SIP device 200 also includes an SIP column 220 including a plurality of potential electrodes (e.g. P1, P2, P3, P4 and P5) arranged along a longitudinal direction of the SIP column 220. The SIP device 200 further includes two current electrodes 230 positioned on opposing ends of the SIP column 220. The method 100 involves obtaining the real-time SIP measurements of the volume of the formation using the SIP device 200. The operation of the SIP device 200 begins with the injection of an electrical current into the formation via the two current electrodes. As this current flows through the volume of the formation, it encounters various resistances depending on the composition of the volume of the formation. These resistances affect flow of the current, which is detected as changes in potential by the potential electrodes 'P1-P5'. By measuring these potentials, the SIP device 200 determines the real conductivity of the matrix material at various points along the SIP column 220. The data collected from these measurements are then used to calculate the real-time RCV of the matrix material, which is used for monitoring the conditions within the formation, specifically for detecting any changes that may indicate the onset of the W/O emulsion formation.

Herein, obtaining the SIP measurements includes obtaining a first set of SIP measurements between two potential electrodes of the plurality of potential electrodes and obtaining a second set of SIP measurements between another two potential electrodes of the plurality of potential electrodes. In one embodiment, the first set of SIP measurements are obtained between potential electrodes 'P1' and 'P5' of the plurality of potential electrodes 'P1-P5'. The first set captures the electrical properties across the entire length of the SIP column 220, providing a view of conductive profile across the formation. The second set of SIP measurements are obtained between the potential electrodes 'P2' and 'P4' of the plurality of potential electrodes 'P1-P5'. The second set provides detail and enhances the understanding of local variations. By obtaining SIP measurements from different pairs of electrodes, the method 100 provides a comprehensive spatial resolution of properties of the formation. Together, these data sets enable the determination of the real-time RCV of the formation.

Generally, in a practical scenario, the method 100 includes placing potential electrodes and current electrodes adjacent to the volume of the formation. Herein, the potential electrodes and the current electrodes are placed at intervals along a borehole adjacent to the volume of the formation or on a ground surface above the volume of the formation. The choice of placement ensures that the electrodes are in positions to effectively capture detailed data on the electrical properties of the formation. The method 100 further includes injecting an alternating electrical current into the formation through the current electrodes. That is, once the electrodes are positioned, the alternating electrical current is injected into the formation through the current electrodes. This injection induces polarization effects within the matrix material, which are then detected and measured by the potential electrodes. The method 100 further includes measuring a set of data via the potential electrodes. Herein, the potential electrodes measure the set of data that, in turn, may be used in determining the real-time RCV of the formation as per embodiments of the present disclosure. Herein, injecting the alternating electrical current and measuring the set of data are executed simultaneously. This simultaneous execution of current injection and data measurement allows for capturing the immediate effects of the electrical current on the formation. The real-time aspect of these measurements ensures that any changes in properties of the formation, such as the formation of W/O emulsions, can be detected.

The set of data collected via the potential electrodes includes other parameters in addition to the real-time RCV. In present embodiments, the set of data include the real-time RCV and at least one selected from the group consisting of an imaginary conductivity, a phase shift and an impedance distribution. The imaginary conductivity measures the component of conductivity that is out of phase with the voltage, providing information about the capacitive properties of the formation materials. The phase shift refers to the delay between the current and voltage responses, providing details about the types of polarizable materials present in the formation. Further, the impedance distribution provides a profile of the resistance to the electrical current within the formation, which can indicate variations in material composition, such as the presence of fluids like water. The comprehensive data set allows for a detailed analysis of properties of the formation, thus helping in detection of the W/O emulsions.

In some embodiments, the method 100 further includes plotting the plurality of RCVs against the water percentage of the plurality of samples. This plotting visualizes the relationship between water content and conductivity changes within the matrix material. The samples used in this analysis cover a range of water concentrations, typically from 0 vol. % to 100 vol. %, thereby covering all possible scenarios. The method 100 also includes determining a critical water concentration for the onset of the W/O emulsion formation. This determination involves analyzing the plotted data to identify specific points where there is a noticeable shift in conductivity that correlates with changes in water content. The critical water concentration is identified as the point at which these shifts become significant, suggesting that beyond this concentration, the conditions may promote the W/O emulsion formation. In some cases, the method 100 further includes determining a range of water percentage for the W/O emulsion formation. This range is established based on the broader analysis of the plotted data, where the beginning and end points of significant conductivity changes are noted. The defined range represents water concentrations that are susceptible to W/O emulsion formation under typical field conditions.

Experimental Data

A portable SIP acquisition system was used in this study. In present implementation, the SIP device 200 of FIG. 2 is utilized for obtaining the real-time SIP measurements of the volume of the formation. In a non-limiting example, a total of 4 stimuli for current injection and 48 nodes for potential measurements were incorporated into the SIP acquisition unit 210. The 48 nodes are designated for 24 measurement channels (2 nodes for each channel). According to the number of the stimuli, the SIP acquisition unit 210 can conduct 4 independent tests simultaneously. In particular, for test purposes, each emulsion sample was hosted in a couple of fabricated acrylic columns to confirm repeatability of the SIP device 200. The SIP column 220 is equipped with several semi-conductor Ag—AgCl electrodes on different axial distances to cover different depths of investigation. The wiring setup for emulsion work was fixed between P1 and P5 (mentioned later as wide SIP) at a distance of 80 mm apart to cover the largest possible depth of investigation and between P2 and P3 (mentioned later as short SIP) at a distance of 20 mm apart to get the shortest possible measurement depth. On the other hand, the wiring setup for the SIP column 220 with the immiscible phases were fixed at P1 and P5 and P2-P4 which covers the interface between both water and oil and P1-P2 which covers the top oil phase. The oil and water were poured in the column at a ratio of 50% of the total volume for each phase and such that the interface is placed in the middle of the column.

For the acquisition parameters, a short survey was sampled in six steps under different sweep frequencies, including 0.1, 1, 10, 100, 1,000 and 10,000 Hz. A 10 kOhm resistor was used for current injection. The main characteristic of frequency-dependent measurements is their dispersion in response to frequency variation, resulting in complex values (real and imaginary parts). This dispersion occurs due to different polarization mechanisms exhibited by the medium under investigation. For example, Nuclear Magnetic Resonance (NMR) measurements rely on the contribution of different polarization mechanisms for the hydrogen atoms and water molecules, such as bulk and surface relaxations. Similarly, the electrical charges can exhibit some polarization mechanisms which results in signal dispersion. In general, the polarization phenomenon associated with electrical fields is a result of the medium capacity to store electrical charges. The ohmic resistance of the material and the quantity of energy lost in the injected current are the real and imaginary components of the complex value of the conductivities. The imaginary conductivity of the medium has a direct relationship to its frequency, increasing with a rise in electric frequency at low values of less than 1 kHz. The polarization effect in frequencies below 1 MHz is governed by a variety of polarization processes, including the Maxwell-Wagner, electrical double layer (EDL) and membrane polarizations.

The main output of the SIP measurement is the complex conductivity described by equation (1) [See: Kimak, C., Ntarlagiannis, D., Slater, L. D., Atekwana, E. A., Beaver, C. L., Rossbach, S., Porter, A., & Ustra, A. (2019)—*Geophysical Monitoring of Hydrocarbon Biodegradation in Highly Conductive Environments, Journal of Geophysical Research: Biogeosciences*, 124 (2), 353-366; Kirmizakis, P., Kalderis, D., Ntarlagiannis, D., & Soupios, P. (2020)—*Preliminary assessment on the application of biochar and spectral-induced polarization for wastewater treatment, Near Surface Geophysics*, 18 (2), 109-122, both incorporated herein by reference in their entireties].

$$\sigma^* = \sigma' + i\sigma'' \quad (1)$$

where, $\sigma'$ and $\sigma''$ are the real and imaginary conductivities, respectively. The magnitude of both parts is related to the absolute magnitude of the complex conductivity, $|\sigma|$ and the phase shift, $\varphi$, through equations (2), (3) and (4).

$$\sigma' = |\sigma|\cos\varphi \quad (2)$$

$$\sigma'' = |\sigma|\sin\varphi \quad (3)$$

$$\varphi = \tan^{-1}\left(\frac{\sigma''}{\sigma'}\right) \quad (4)$$

Further, for emulsion preparation, Arabian medium crude oil was used as the continuous phase, while 3% KCl brine was used as the discontinuous aqueous phase. Besides the blank brine and crude samples, six different W/O emulsions were prepared: 90% oil-10% water (90/10), 70% oil-30% water (70/30), 50% oil-50% water (50/50) and 30% oil-70% water (30/70). Each sample was investigated in two separate columns to check the repeatability of the SIP measurements. A careful preparation procedure was followed to achieve homogeneous and stable emulsions. 30 minutes of steering time at 5500 rpm was performed. The water-in-oil type was checked by 2 methods; electrical conductivity and fluids drops. The electrical conductivity showed very low value (around 1 µS/cm) while the resistivity showed values greater than 500,000 ohms which confirmed that oil is the continuous phase. On the other hand, oil drops merged in a miscible way, whereas the water drop migrated or moved immiscibly in all the emulsions. The stability of the emulsions was monitored for two weeks and showed no phase segregation. Table 1 below illustrates the compositions, and pH measurements. Further, FIGS. 3A-3D depict pictures of samples 2-5, respectively.

TABLE 1

Emulsions composition and properties.

| Sample # | 1 | 2 | 3 | 4 | 5 | 6 |
|---|---|---|---|---|---|---|
| Oil Vol % | 100 | 90 | 70 | 50 | 30 | 0 |
| Water Vol % | 0 | 10 | 30 | 50 | 70 | 100 |
| pH | 5.158 | 5.210 | 5.257 | 5.333 | 5.772 | 6.872 |

Figure 4:
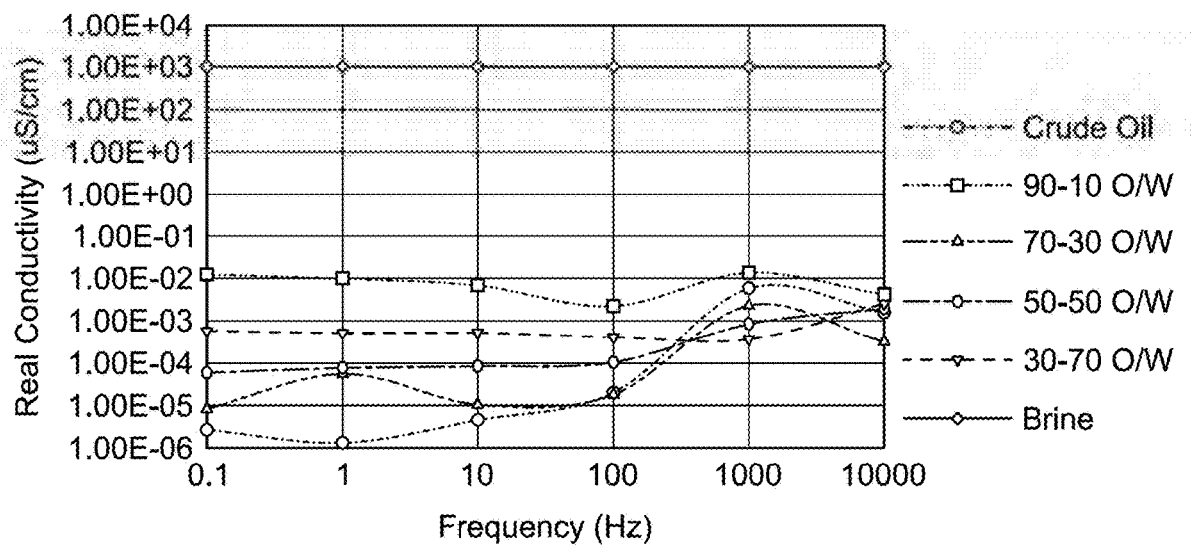
FIG. 4 illustrates real conductivity measured by short SIP measurements for different emulsion compositions, according to certain embodiments.
Figure 5:
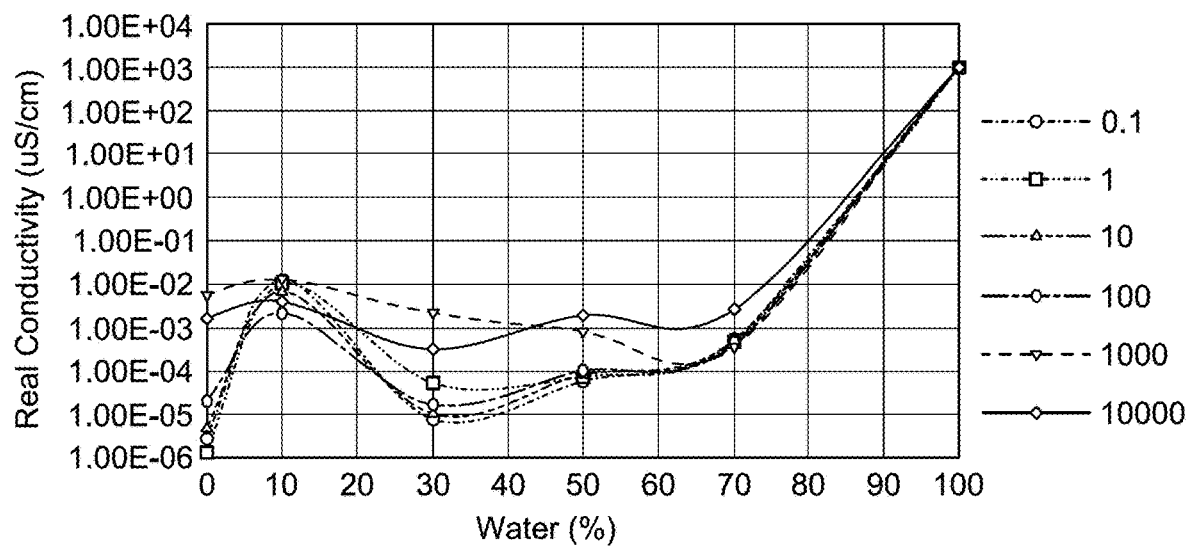
FIG. 5 illustrates real conductivity measured by short SIP measurements for different water percentages, according to certain embodiments.

It may be noted that both short and wide (long) SIP measurements showed significant variation in response to the change in the emulsion composition. FIGS. 4 and 5 illustrate the real conductivity measured by the short SIP measurements (electrodes (P2-P3)) for different emulsion compositions and water percentages, respectively.

In FIG. 5, consider 0.1 Hz for example. The real conductivity value (RCV) for crude oil can correspond to an initial value of a matrix material when the volume of the formation is dry or a value of the matrix material mixed with some naturally present water. As the water percentage increases from 0 vol. % to 10 vol. %, the RCV increases dramatically by at least three orders of magnitude. Then the RCV decreases rapidly by about three orders of magnitude as the water percentage increases from 10 vol. % to 30 vol. %. Then the RCV increases again as the water percentage increases from 30 vol. % to 100 vol. %.

That is to say, a local maximum of the RCV exists between 0 vol. % and 30 vol. %, for example between 5 vol. % and 15 vol. %, or around 10 vol. %. More data around 10 vol. % would be helpful to accurately identify the local maximum of the RCV, which however may not be necessary for the purposes of the present application. That is, the onset of water-in-oil emulsion (W/O) formation does not have to coincide with the local maximum of the RCV. As discussed earlier, a user may determine that the onset of W/O formation occurs when the RCV first becomes 100 times of its initial value for example.

Additionally, other plots in FIG. 5 representing 1 Hz, 10 Hz and 100 Hz show similar trends although the exact RCV values may differ. By contrast, in the case of 1000 Hz or 10000 Hz, the RCV increases by less than one order of magnitude as the water percentage increases from 0 vol. % to 10 vol. %. While a local maximum of the RCV value may seem to exist for 1000 Hz and 10000 Hz, the increase in the RCV value is not as pronounced as shown in 0.1 Hz, 1 Hz, 10 Hz and 100 Hz.

Figure 6:
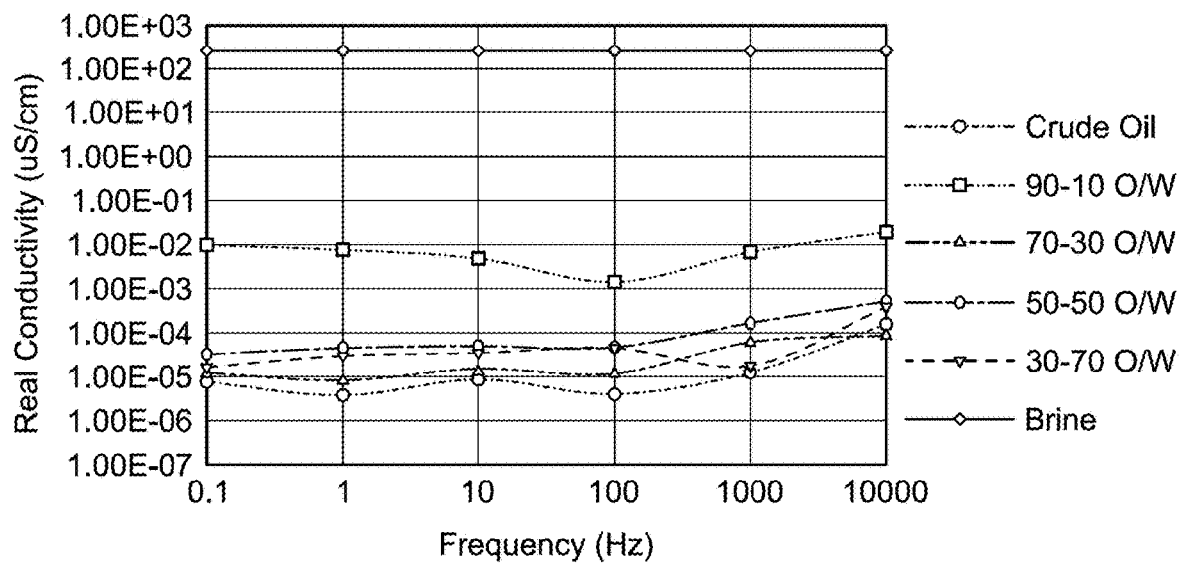
FIG. 6 illustrates real conductivity measured by wide SIP measurements for different emulsion compositions, according to certain embodiments.
Figure 7:
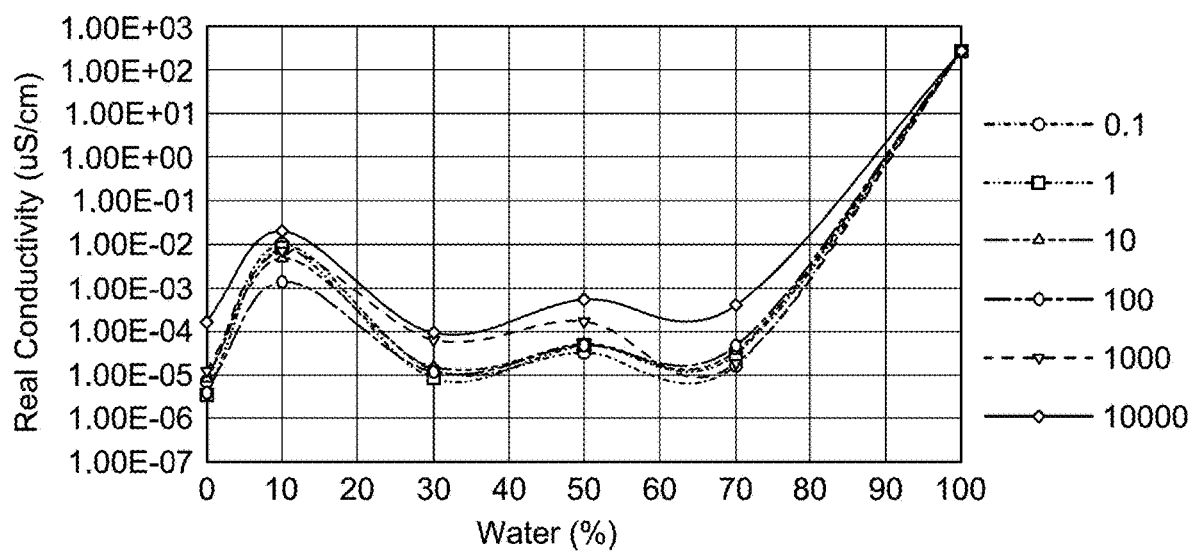
FIG. 7 illustrates real conductivity measured by wide SIP measurements for different water percentages, according to certain embodiments.

Therefore, to detect the onset of W/O formation, a single frequency or a plurality of discrete frequencies can be used. The single frequency may range from 0.1 Hz to 100 Hz, preferably 1 Hz to 50 Hz, preferably 5 Hz to 25 Hz, preferably 10 Hz to 20 Hz or any values therebetween. Similarly, the plurality of discrete frequencies can be selected from a range of 0.1 Hz to 100 Hz, preferably 1 Hz to 50 Hz, preferably 5 Hz to 25 Hz, preferably 10 Hz to 20 Hz or any values therebetween. It should be understood that a frequency sweep is not necessary here, but a user may still choose to do a frequency sweep over a range of 0.1 Hz to 100 Hz, preferably 1 Hz to 50 Hz, preferably 5 Hz to 25 Hz, preferably 10 Hz to 20 Hz or any values therebetween. FIGS. 6 and 7 illustrate the real conductivity measured by the wide SIP measurements (electrodes (P1-P5)) for different emulsion compositions and water percentages, respectively. Due to the extremely high resistivity of the crude, the injected current was facing high resistance to travel between the stimuli which results in larger variation in the short SIP measurement (P2-P3) than the wide SIP measurement. Moreover, the results also showed that a low frequency range (e.g., 0.1-100 Hz) is the suitable range for monitoring the changes in the emulsion composition. The real conductivity exhibited a consistent increase with the rise in the content of the conductive brine for the emulsion samples #3 (70/30), 4 (50/50) and 5 (30/70). On the other hand, the sample #2 (90/10) showed distinctly higher real conductivity values than all other compositions. This can be attributed to the larger particle size found for that sample which will be discussed later.

Particularly in FIG. 7, consider 0.1 Hz or 1 Hz for example. The RCV increases by at least two orders of magnitude as the water percentage increases from 0 vol. % to 10 vol. %. Similar to FIG. 5, while a local maximum of the RCV value may seem to exist for 10000 Hz, the increase in the RCV value is not as pronounced as shown in 0.1 Hz.

Figure 8:
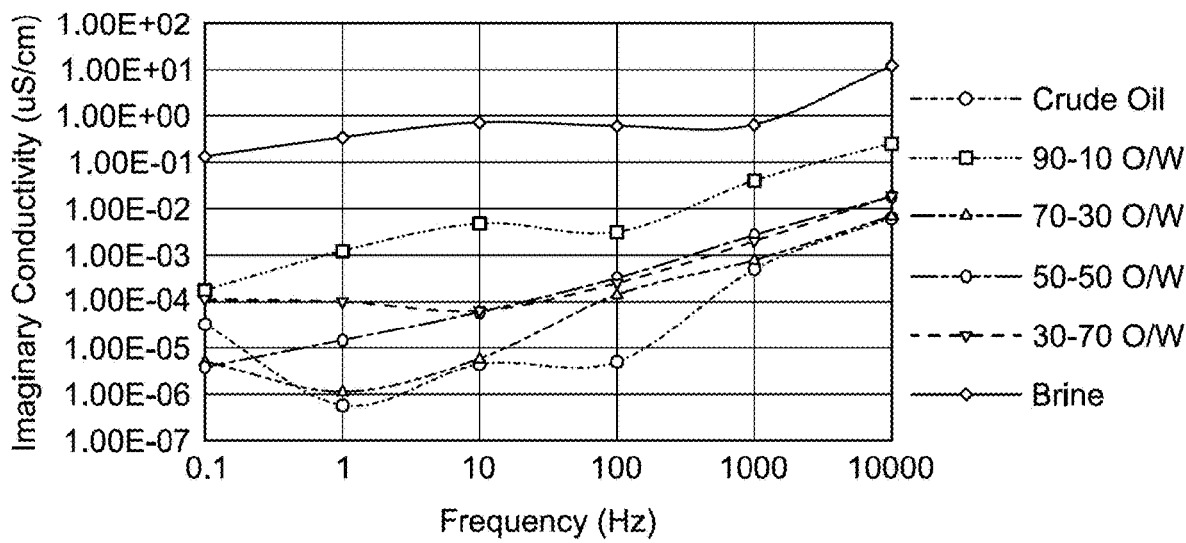
FIG. 8 illustrates imaginary conductivity measurements for different emulsion compositions by short SIP measurements, according to certain embodiments.
Figure 9:
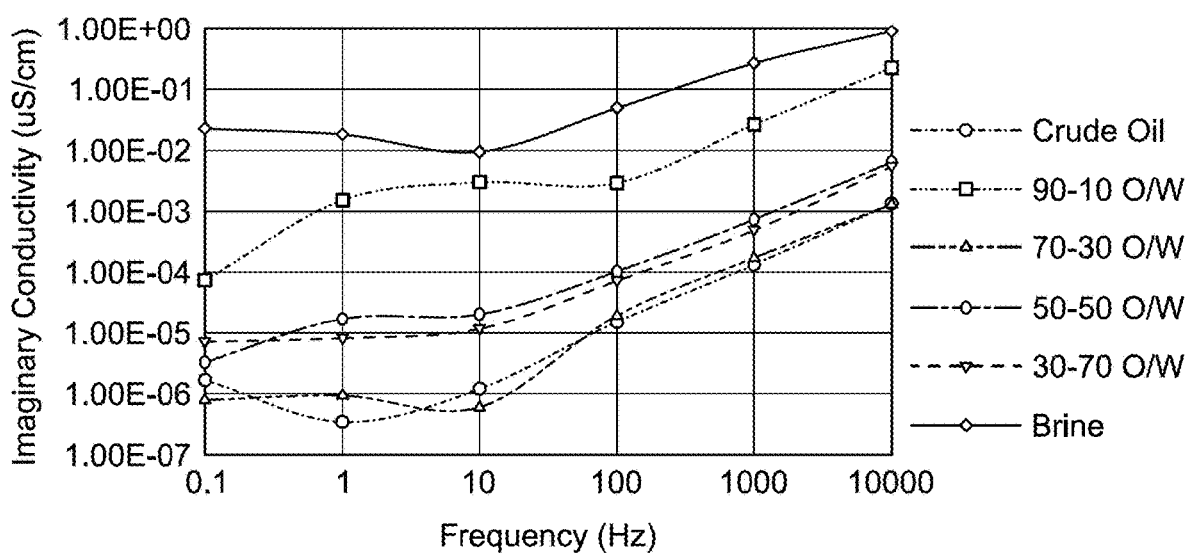
FIG. 9 illustrates imaginary conductivity measurements for different emulsion compositions by wide SIP measurements, according to certain embodiments.

Further, FIGS. 8 and 9 illustrate the imaginary conductivity measurements for different emulsion compositions by the short SIP measurements (electrodes (P2-P3)) and the wide SIP measurements (electrodes (P1-P5)), respectively. As may be seen, the imaginary conductivity measurements showed clear dispersion (slope change) in response to the frequency variation. In general, imaginary conductivity measures the polarization response associated with changing the frequency. More polarization is expected to occur while increasing the frequency which has been observed in the plots. However, the sample #2 (90/10) showed larger imaginary values than the rest of the samples, like the real conductivity trend.

Figure 10:
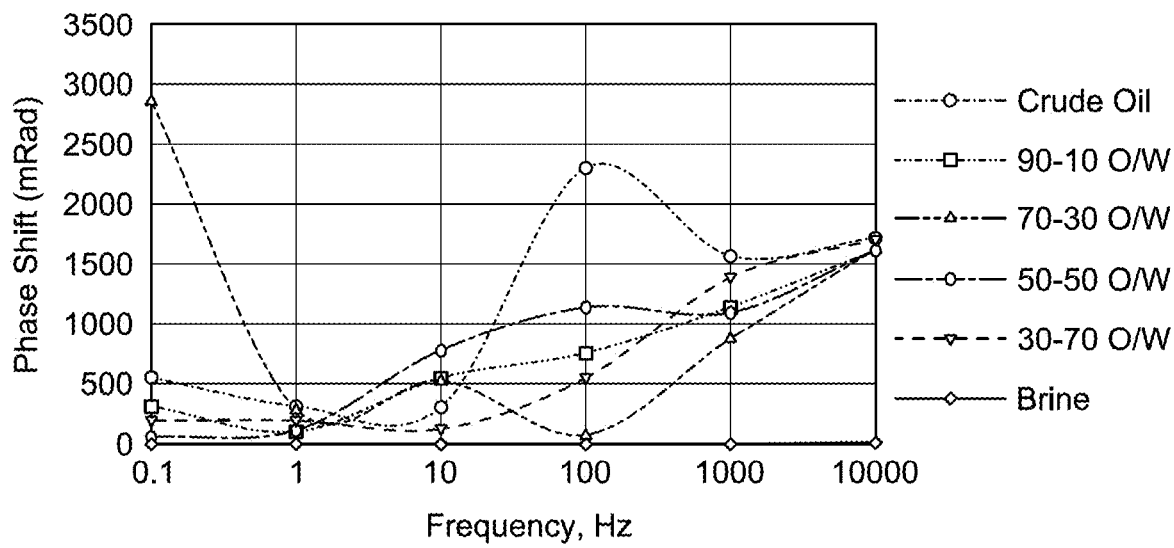
FIG. 10 illustrates phase shift measurements for different emulsion compositions by short SIP measurements, according to certain embodiments.
Figure 11:
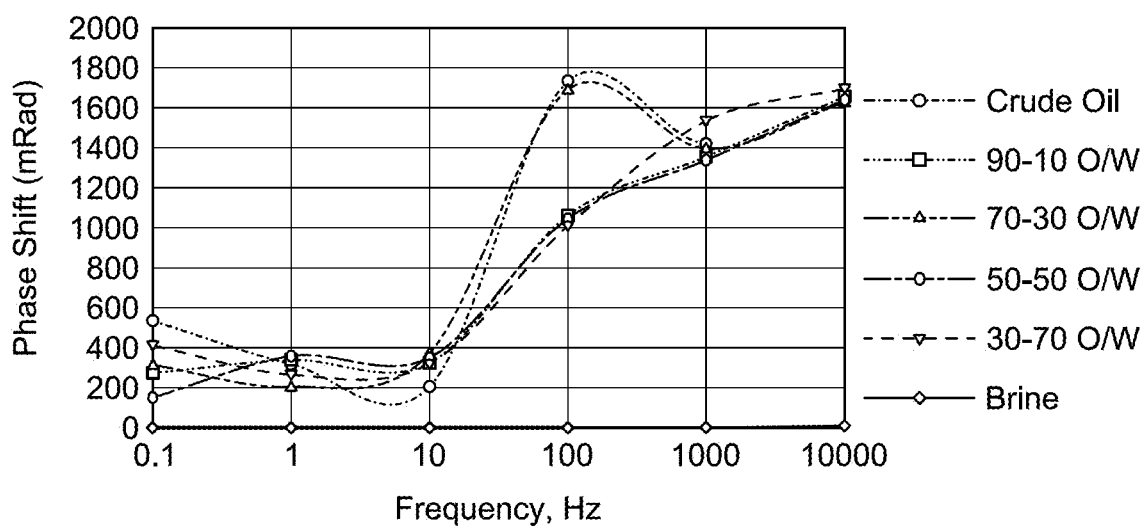
FIG. 11 illustrates phase shift measurements for different emulsion compositions by wide SIP measurements, according to certain embodiments.

Furthermore, FIGS. 10 and 11 illustrate phase shift measurements for different emulsion compositions by the short SIP measurements (electrodes (P2-P3)) and the wide SIP measurements (electrodes (P1-P5)), respectively. The phase shift represents the angle used to generate the complex conductivity values and it is mainly affected by the presence of multiple phases within the medium. As may be seen, the phase shift results showed inconclusive trends for all the samples except the brine which showed very low values (close to zero). Since the brine represents a single fluid phase with high conductivity values compared to the other samples, its phase shift measurements showed values of around zero. This also indicates that there is not much polarization exhibited in the brine.

Figure 12:
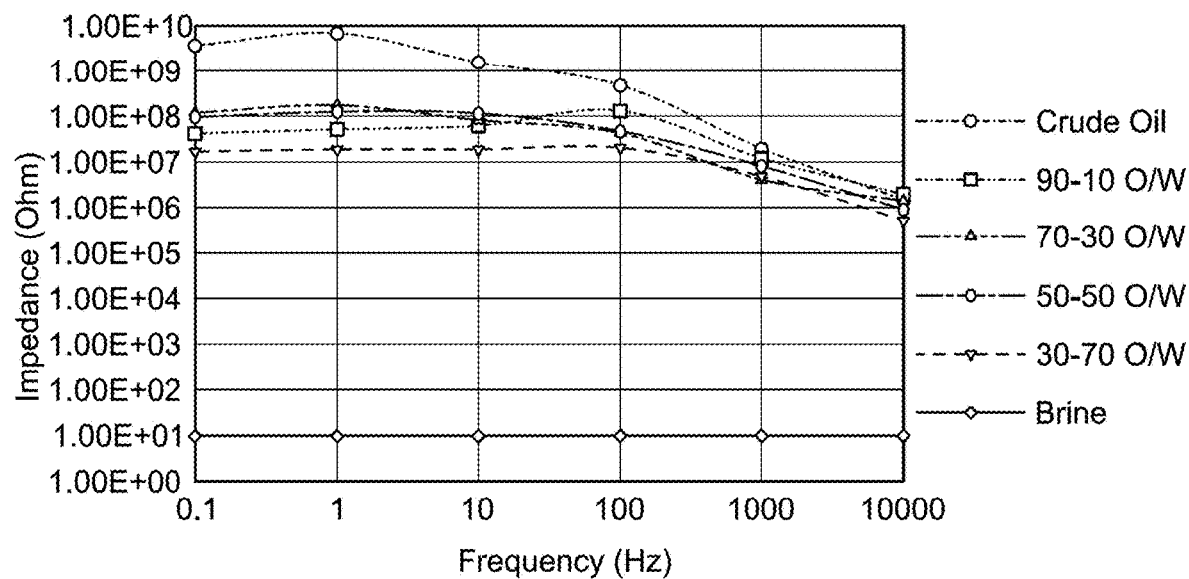
FIG. 12 illustrates impedance of all emulsion samples on semi-log scale by short SIP measurements, according to certain embodiments.
Figure 13:
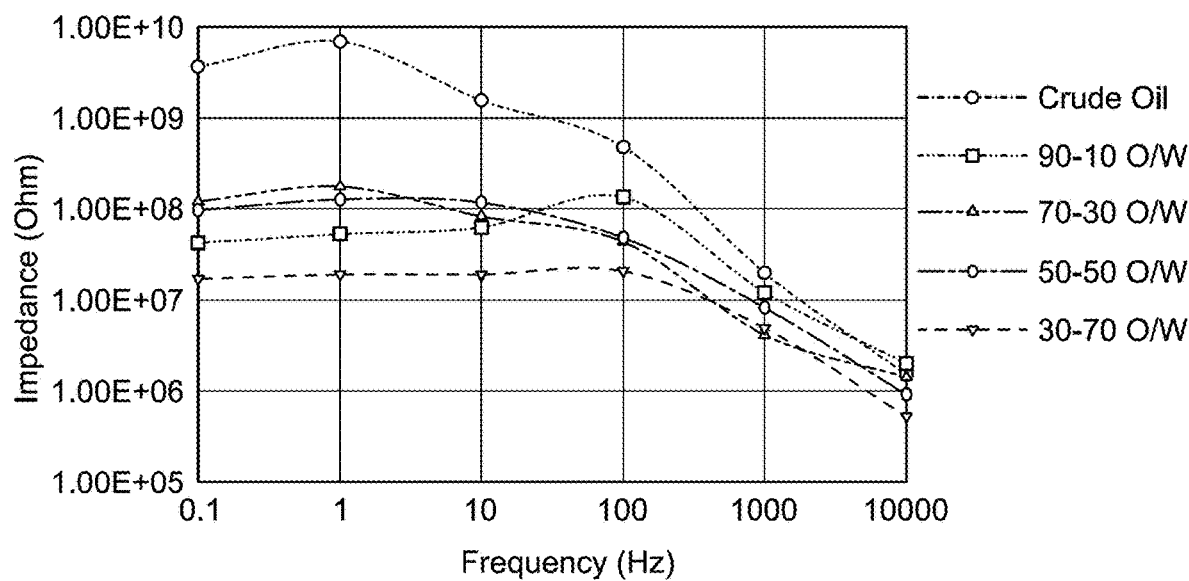
FIG. 13 illustrates impedance of emulsion samples excluding brine on a smaller semi-log scale by short SIP measurements, according to certain embodiments.
Figure 14:
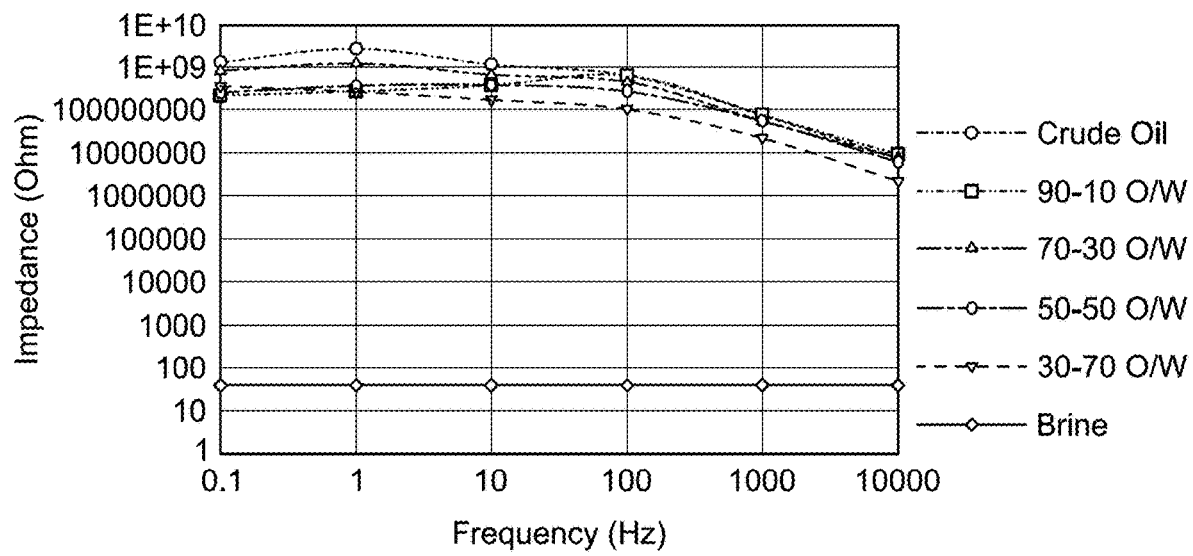
FIG. 14 illustrates impedance of all emulsion samples on semi-log scale by wide SIP measurements, according to certain embodiments.
Figure 15:
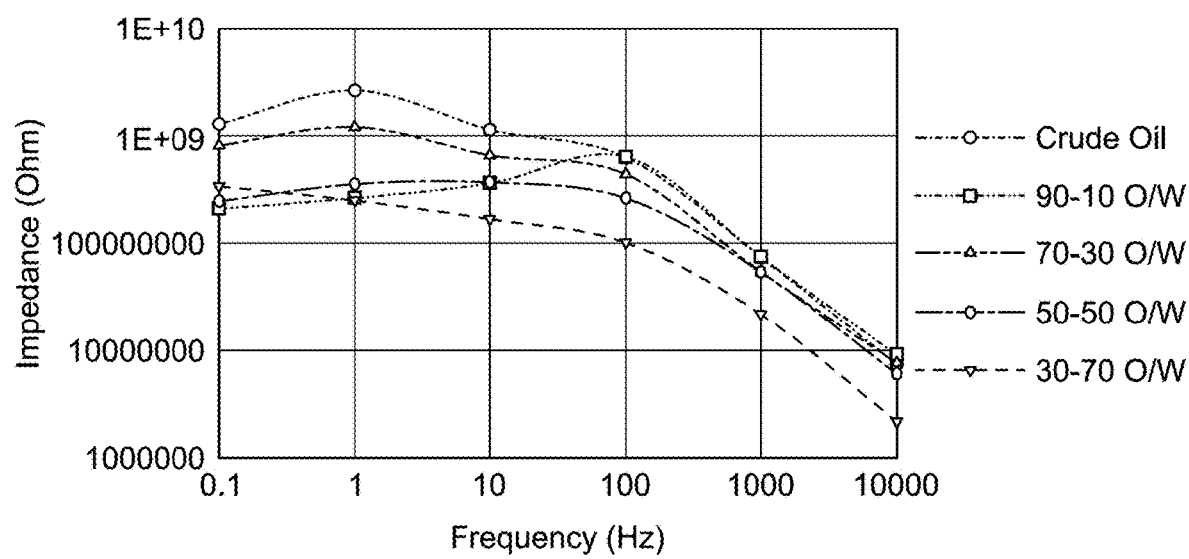
FIG. 15 illustrates impedance of emulsion samples excluding brine on a smaller semi-log scale by wide SIP measurements, according to certain embodiments.

Moreover, FIG. 12 illustrates impedance of all the samples on semi-log scale using the short SIP measurements (P2-P3), while FIG. 13 illustrates the impedance of the crude and the emulsion on smaller semi-log scale. On the other hand, FIGS. 14 and 15 illustrate the same respective curves but for the long SIP measurements (P1-P5). Herein, the impedance measurement is related to the resistivity of the medium. The crude oil and emulsion samples showed significantly higher impedance values than the brine and the measurement was observed to decline with elevating the frequency. Increasing the frequency means bombarding the system with more electrical current which induces extra conductivity and reduces the impedance. This phenomenon was observed in the crude and the emulsion samples whereas the brine showed almost constant impedance value.

Figure 16:
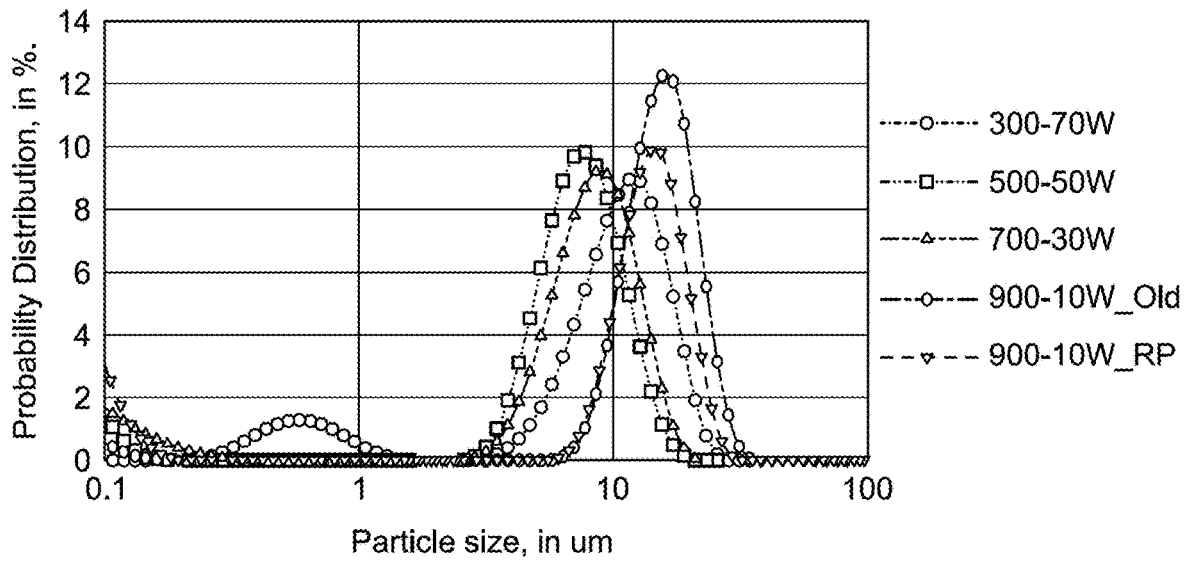
FIG. 16 illustrates particle size probability distribution of all emulsion samples using laser particle size analyzer, according to certain embodiments.
Figure 17:
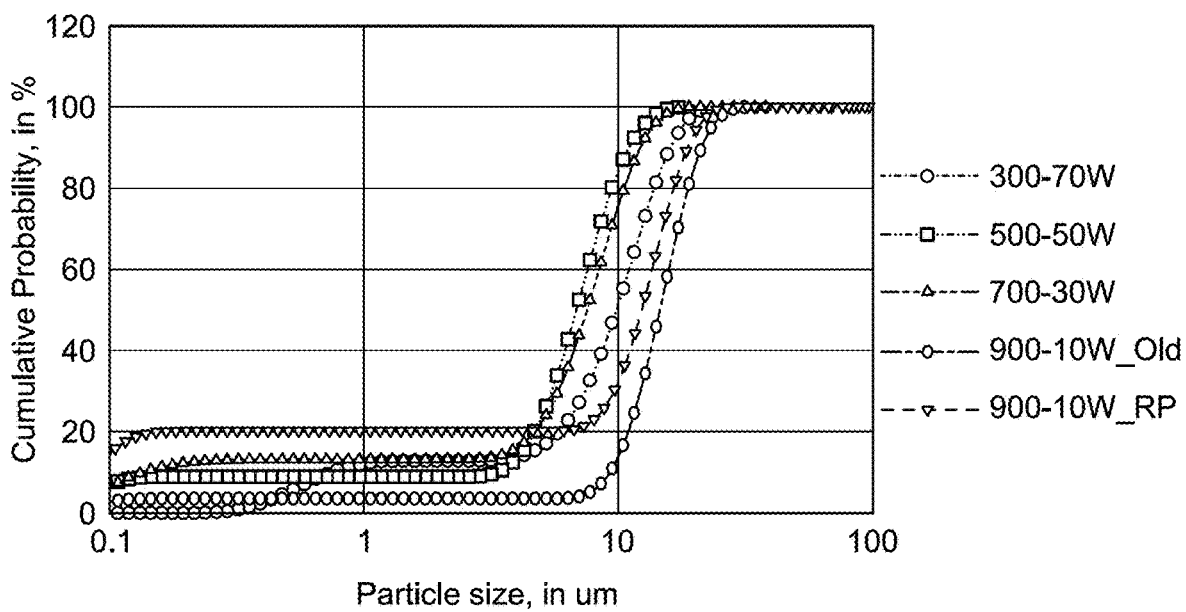
FIG. 17 illustrates cumulative particle size probability distribution of all emulsion samples using laser particle size analyzer, according to certain embodiments.

Further, FIG. 16 illustrates particle size probability distribution of all the emulsion samples. FIG. 17 illustrates cumulative particle size distribution of all the emulsion samples. Herein, to investigate the particle size of the emulsions, a laser particle size analyzer was used. The measurement showed that the sample #2 (90/10) emulsion has a significantly larger particle size than the other emulsions, which explains the high real conductivity values and not following the relationship between the SIP and the brine content. The mean particle size of the sample #2 was found to be about twice the mean particle size of the sample #4 (50/50) and sample #3 (70/30). To confirm the validity of the sample #2 (90/10) particle size measurement, a repeat sample was prepared and measured. Both samples showed similar particle sizes. The mean particle size of different emulsion composition was extracted and presented in Table 2.

TABLE 2

Mean particle sizes of different emulsions obtained from the peaks of the different curves in FIG. 16

| Emulsion Composition | Mean Particle Size, in μm |
|---|---|
| 30 O-70 W | 10.9679 |
| 50 O-50 W | 8.1405 |
| 70 O-30 W | 8.9910 |
| 90 O-10 W_Main | 16.3212 |
| 90 O-10 W_Repeat | 16.7734 |

Figure 18:
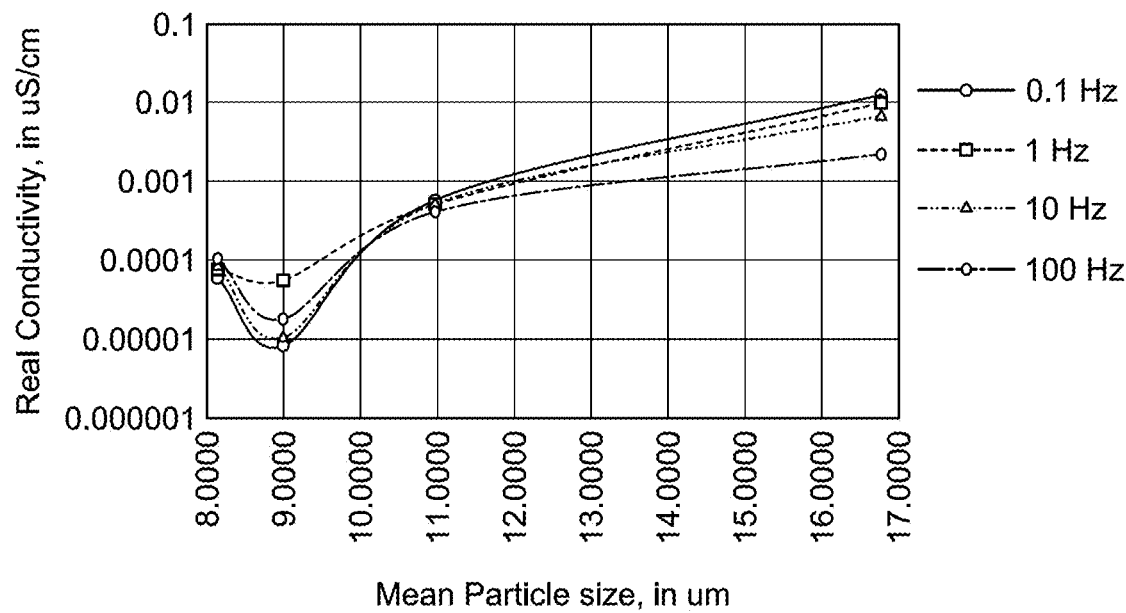
FIG. 18 illustrates a direct relationship between particle size and logarithm of real conductivity, according to certain embodiments.

The SIP results showed that the real conductivity is the most sensitive to composition of the emulsion and the variation of the particle size. FIG. 18 illustrates a direct relationship between particle size and logarithm of the real conductivity. This deduces the effectiveness of the SIP measurement in detecting early signs of emulsion formation. During early stages of emulsion formation, the size of the water inclusions is relatively large which helps the SIP to detect it via the real conductivity measurement. As more water is produced and larger water concentration is evolved in the emulsions, the particle size decreases, and the real conductivity drops consequently.

Therefore, although the real conductivity proved its efficiency in detecting the water in oil emulsions at low water concentrations, it needs further analysis to obtain a quantitative relationship between SIP and water content in the emulsions. The study showed that both particle size and water content play a role in the SIP response, and both need to be considered to establish a relationship to quantify the water content in the emulsion. However, detecting the emulsions at low water concentrations should always be the primary goal of monitoring the formation of emulsion in order to design the remedial and the mitigation measures related to emulsions issues.

Figure 19:
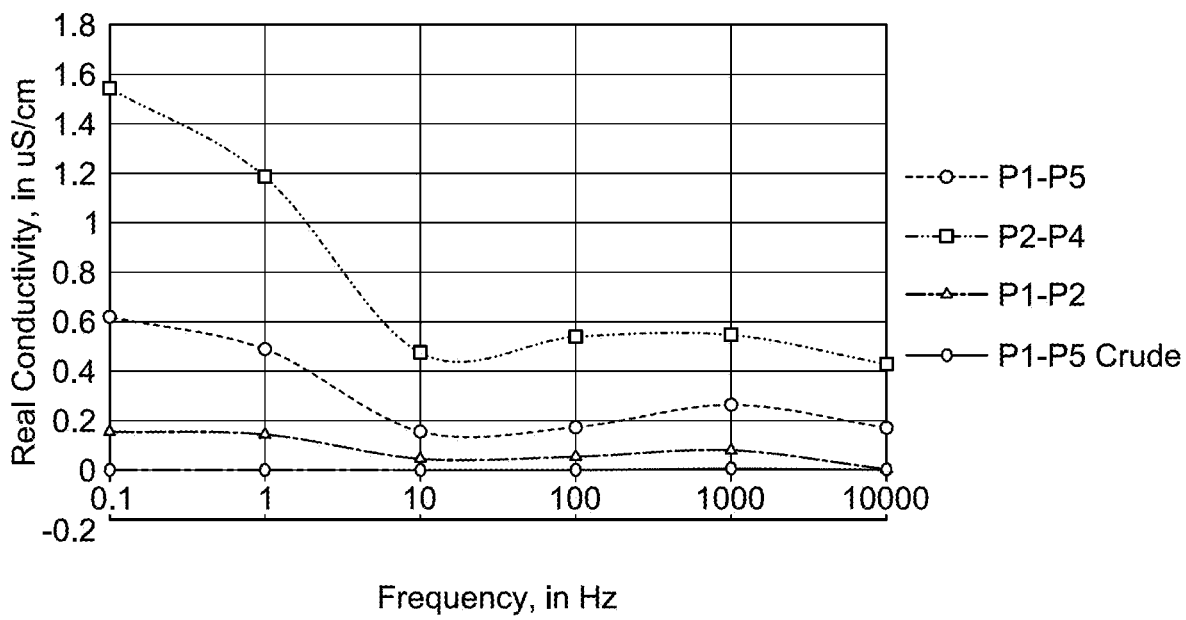
FIG. 19 illustrates real conductivity results for multiphase fluid compared to pure crude measurement, according to certain embodiments.

FIG. 19 illustrates the real conductivity results compared to the pure crude measurement. The results showed a very distinctive response towards the presence of multiple immiscible fluids with contrast in their electrical properties. Although all channels showed significant variation in the SIP measurements compared to the pure crude, channels P1-P5 and P2-P4, which are covering the interface between both fluids, were particularly affected by the multiphase presence. The real conductivity showed a significant increase on channels P1-P5 and P2-P4 across the whole frequency bandwidth and the largest change was observed at low frequencies; 0.1 and 1 Hz.

Figure 20:
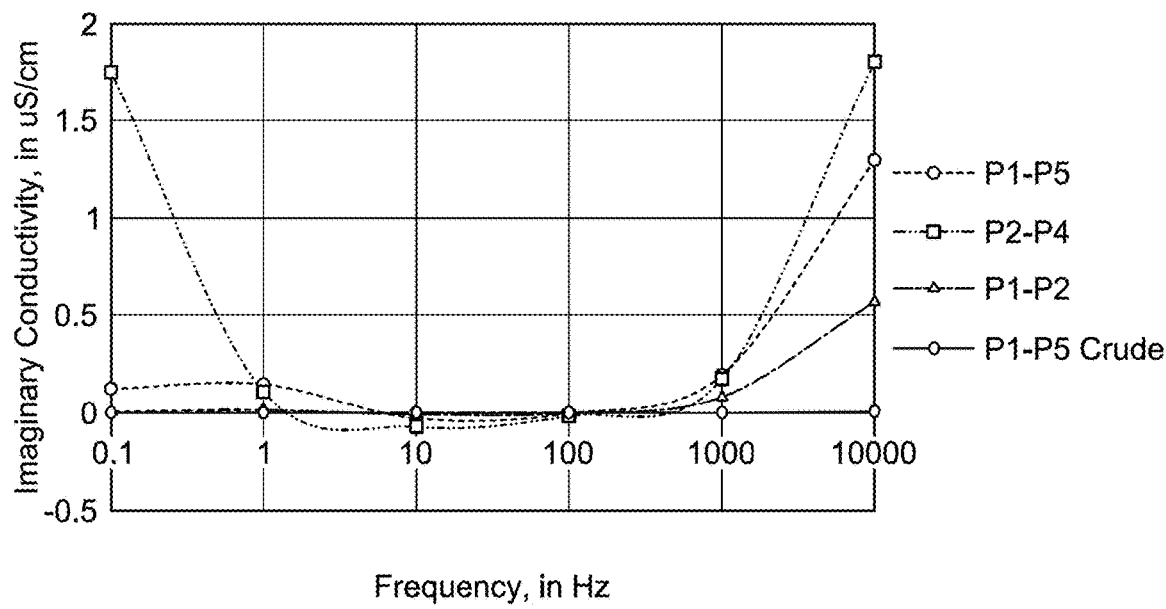
FIG. 20 illustrates imaginary conductivity results for multiphase fluid compared to pure crude measurement, according to certain embodiments.

FIG. 20 illustrates the imaginary conductivity results of the multiphase system in comparison with the crude measurement. For the imaginary conductivity which results from the polarization induced by the presence of multiple media with large differences in their electrical conduction, a significant rise in the value was observed at very large frequency: 10,000 Hz. On the contrary, there was not much of variation in the imaginary conductivity measured by the channel P1-P5 between the crude and the multiphase fluid at low frequencies. The appearance of the variation at high frequency only indicates that the need to bombard the multiphase system with high current intensity to feel the polarization occurring at the interface between the phases at relatively large volumes.

Figure 21:
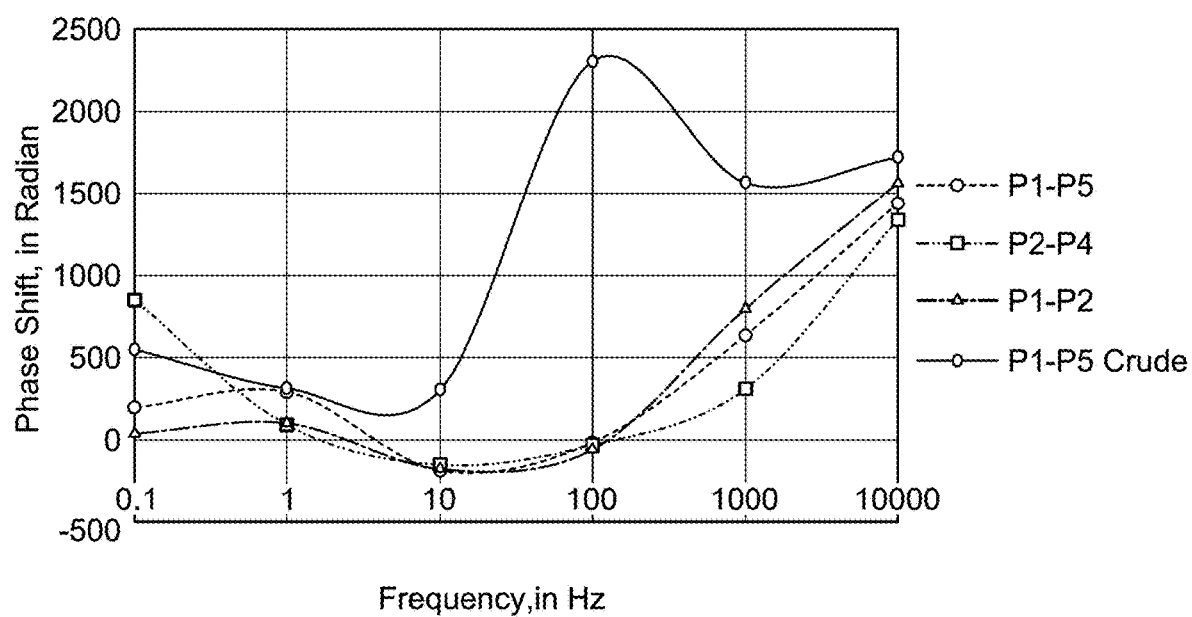
FIG. 21 illustrates phase shift results for multiphase fluid compared to pure crude measurement, according to certain embodiments.

FIG. 21 illustrates phase shift results for the segregated phases compared to the bare crude. As it was deduced for the emulsions results, phase shift is not a conclusive response to the presence of the oil and water whenever the extremely resistive oil is forming a continuous phase. For the multiphase fluid investigation, phase shift showed low variation at frequencies; 0.1, 1, 1000 and 10,000 Hz. However, it significantly dropped around 2300 radian at 100 Hz. This frequency can be used as an excellent detector for the interface between oil and water.

Figure 22:
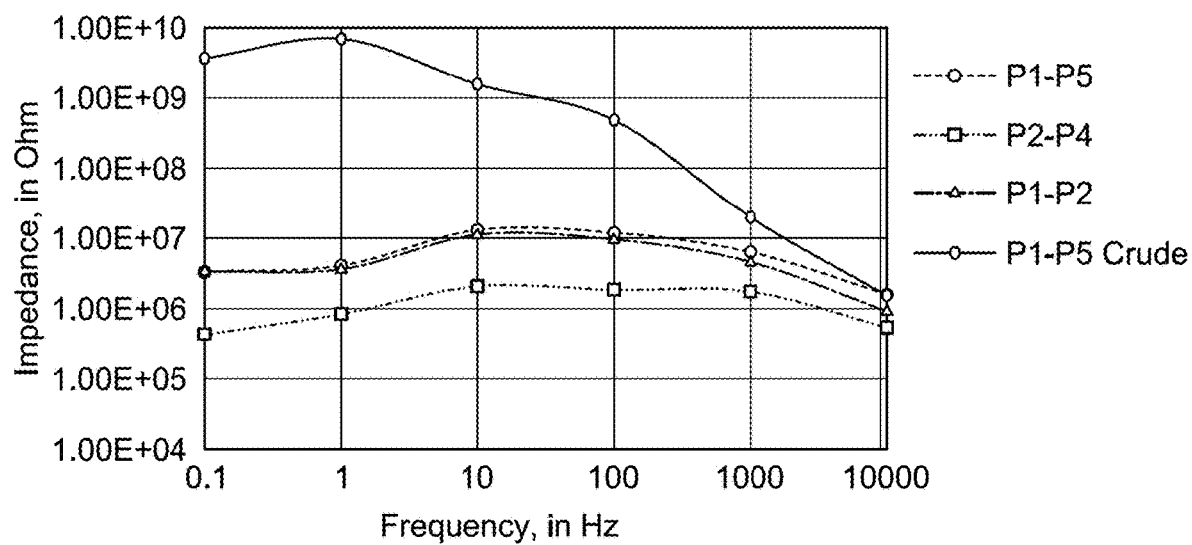
FIG. 22 illustrates impedance results for multiphase fluid compared to pure crude measurement, according to certain embodiments.

FIG. 22 illustrates impedance results for the multiphase fluid system compared to the crude oil on log-log scale. The impedance showed good response to immiscible water and oil within the investigation volume. The results showed a steep drop in the impedance at low frequency range. A decline of around 3 orders of magnitude was observed at 0.1 Hz for all the channels acquired. However, the variation in impedance declines with increasing frequency and it almost diminishes at 10,000 Hz. Therefore, low frequency should be utilized for using the impedance as a multiphase flow detector (less than 100 Hz preferably).

The SIP technique of the present disclosure may effectively detect and analyze different types and concentrations of emulsions. Herein is described the use of a portable SIP acquisition module and fabricated acrylic columns to investigate the relationship between water concentration in the emulsion and SIP signals. The results showed that the real conductivity and imaginary conductivity increased with increasing water concentration for emulsions with compositions of (70/30), (50/50), and (30/70). However, the emulsion with a composition of (90/10) exhibited significantly higher values of real conductivity and imaginary conductivity (order of magnitudes) compared to other compositions. This can be attributed to the larger particle size in the (90/10) emulsion compared to the other emulsion compositions. On the other hand, no conclusive relationship was found between the phase shift and the emulsion type. However, the brine showed flat line, close to zero phase shift. Furthermore, the impedance showed inverse relationship with the water content which agrees with the physical meaning of the impedance which can be described as electrical resistance. Also, it was found that the impedance decreases with increasing the frequency which can be explained by inducing extra conductivity by bombarding the system with the electrical current at high frequency.

Further, the laser particle size analyzer was used to investigate the particle sizes of the emulsions. The mean size of the (90/10) particles (~16.7 μm) was found to be twice the size of the (70/30) and (50/50) (~8.99 μm and 8.14 μm respectively). The size of (30/70) particles was found larger than the (70/30) and (50/50) samples with value of 10.97 μm. Plotting the real conductivity versus the mean particle size on semi-log scale showed some correlation between both parameters. The study demonstrated that the SIP technique could detect oil in water emulsions with water concentrations as low as 10%. However, to find a quantitative relationship, both water content and mean particle size of the emulsion should be considered.

Furthermore, for multiphase fluid assessment, the results showed excellent results which enables the SIP technique to be one of the key measurements for multiphase detection in both storage tanks and flowlines. All results showed significant variation by comparing the results of the multiphase measurements to the pure crude oil. Real conductivity and impedance can be used at low frequencies. Within the present experimental frame, the maximum drop in the impedance was observed at 0.1 Hz which reached 3 orders of magnitudes. In contrast, the imaginary conductivity showed the largest variation at high frequencies, at 10,000 Hz specifically. On the other hand, phase shift showed the least conclusive results due to the extreme resistivity of the oil. However, it showed very clear variation at 100 Hz which can be used for multiphase fluid detection.

To sum up, real and imaginary conductivities, phase shift and impedance, are the main measurements obtained during the measurements. In a column set up, several water compositions in oil emulsions were investigated to find a qualitative relationship between the water concentration in the oil-in-water (O/W) emulsion and SIP response. Besides pure crude and brine, two columns for each of four different compositions of O/W emulsions were tested; 90% oil-10% water (90/10), 70% oil-30% water (70/30), 50% oil-50% water (50/50) and 30% oil-70% water (30/70). In addition, a separate column for both immiscible phases; oil and water, with a ratio of 50% of each phase, was investigated to represent a multiphase flow. The SIP acquisition was set at 6 different frequencies: 0.1, 1, 10, 100, 1000 and 10000 Hz. There was a consistent increase in the real conductivity at the frequency range of (0.1 Hz-100 Hz) by increasing the water concentration in the emulsions for the samples (70/30), (50/50) and (30/70). However, the (90/10) sample showed a significant increase in the real conductivity with four orders of magnitude greater than the values for the crude oil and one order of magnitude higher than the values for the highest water concentration corresponding to the sample (30/70). This illustrates the excellent detectability of the SIP for emulsion formation at early stages. Moreover, the same trend in the real conductivity for the (90/10) sample was observed in the imaginary conductivity. This trend can be attributed to the large particle size associated with the (90/10) sample compared to the others. This was confirmed by a laser particle size analyzer which showed that (90/10) sample has a mean particle size of 18 μm compared to 9 μm for the (70/30). On the other hand, the results for the column with multiphase immiscible fluids showed very clear variation on all SIP measurements compared to the single-phase crude measurements. Therefore, the SIP technique can be used to detect oil in water emulsions at water concentrations as low as 10% which raises the alarm for the necessity of remedial actions.

Water breakthroughs during oil production can lead to emulsion formation and multiphase flow. Both can pose various implications to the production process within both upstream and downstream systems, such as ceasing oil flow, pores blockage, pipes corrosion, and inducing significant treatment, separation, and disposal costs. There are different types of emulsions. However, at early stages of water production, the W/O emulsions is the common type and hence it is the focus of the present disclosure. In the preset disclosure detecting early signs of water breakthrough and emulsion formation trigger remedial actions. The present disclosure provides the method 100 to use the SIP technique to track the formation of water in oil emulsions in oil and gas reservoirs. The method 100 provides the use of the SIP technique to track the multiphase flow in tubing, flowlines, and separator tanks.

The method 100 of the present disclosure can be used as real-time monitoring to detect early signs of emulsions formation using SIP real conductivity. In the environment of an oil production process, the formation of these emulsions can vary dynamically with the conditions of the reservoir and the characteristics of the extracted fluids. Emulsions are of particular concern in the oil industry due to their potential to impact the efficiency of the oil recovery process and the integrity of the infrastructure used in this process. The real-time detection of the onset of the W/O emulsion formation enables timely interventions that can optimize the production process and mitigate potential complications associated with emulsions. Such effective management of emulsions can significantly reduce downtime caused by equipment blockages or failures and decrease the costs associated with additional processing requirements. By managing emulsions effectively, the overall efficiency of the oil recovery process is improved, ensuring a higher yield and quality of the extracted oil.

Figure 23:
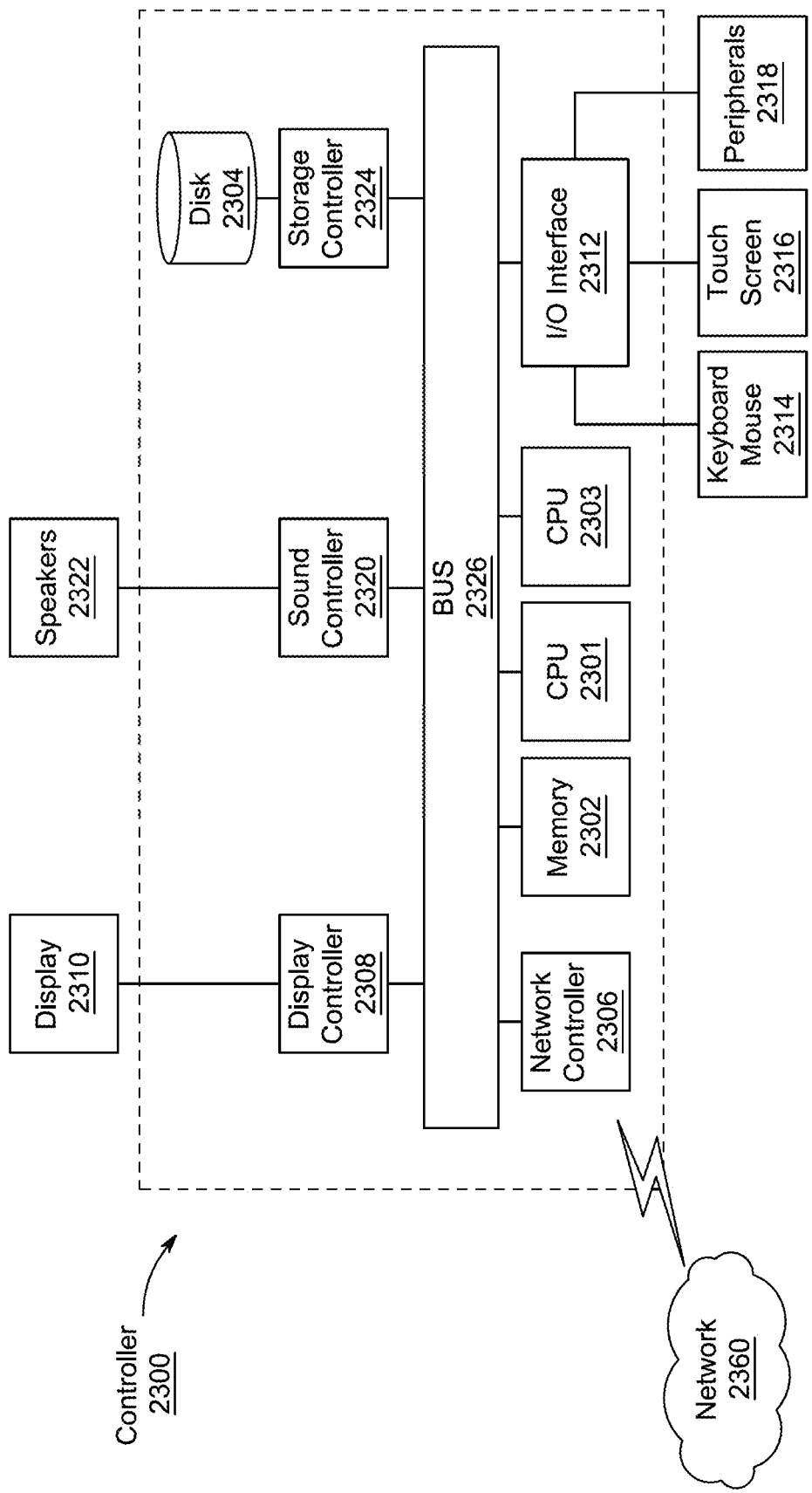
FIG. 23 is an illustration of a non-limiting example of details of computing hardware used in the computing system, according to certain embodiments.

Next, further details of the hardware description of the computing environment according to exemplary embodiments is described with reference to FIG. 23. In FIG. 23, a controller 2300 is described in which the controller 2300 is a computing device which includes a CPU 2301 which performs the processes described above/below. The process data and instructions may be stored in memory 2302. These processes and instructions may also be stored on a storage medium disk 2304 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with CPU 2301, 2303 and an operating system such as Microsoft Windows 7, Microsoft Windows 8, Microsoft Windows 10, UNIX, Solaris, LINUX, Apple MAC-OS, and other systems known to those skilled in the art.

The hardware elements in order to achieve the computing device may be realized by various circuitry elements, known to those skilled in the art. For example, CPU 2301 or CPU 2303 may be a Xenon or Core processor from Intel of America or an Opteron processor from AMD of America, or may be other processor types that would be recognized by one of ordinary skill in the art. Alternatively, the CPU 2301, 2303 may be implemented on an FPGA, ASIC, PLD or using discrete logic circuits, as one of ordinary skill in the art would recognize. Further, CPU 2301, 2303 may be implemented as multiple processors cooperatively working in parallel to perform the instructions of the inventive processes described above.

The computing device in FIG. 23 also includes a network controller 2306, such as an Intel Ethernet PRO network interface card from Intel Corporation of America, for interfacing with network 2360. As can be appreciated, the network 2360 can be a public network, such as the Internet, or a private network such as an LAN or WAN network, or any combination thereof and can also include PSTN or ISDN sub-networks. The network 2360 can also be wired, such as an Ethernet network, or can be wireless such as a cellular network including EDGE, 3G, 4G and 5G wireless cellular systems. The wireless network can also be WiFi, Bluetooth, or any other wireless form of communication that is known.

The computing device further includes a display controller 2308, such as a NVIDIA GeForce GTX or Quadro graphics adaptor from NVIDIA Corporation of America for interfacing with display 2310, such as a Hewlett Packard HPL2445w LCD monitor. A general purpose I/O interface 2312 interfaces with a keyboard and/or mouse 2314 as well as a touch screen panel 2316 on or separate from display 2310. General purpose I/O interface also connects to a variety of peripherals 2318 including printers and scanners, such as an OfficeJet or DeskJet from Hewlett Packard.

A sound controller 2320 is also provided in the computing device such as Sound Blaster X-Fi Titanium from Creative, to interface with speakers/microphone 2322 thereby providing sounds and/or music.

The general purpose storage controller 2324 connects the storage medium disk 2304 with communication bus 2326, which may be an ISA, EISA, VESA, PCI, or similar, for interconnecting all of the components of the computing device. A description of the general features and functionality of the display 2310, keyboard and/or mouse 2314, as well as the display controller 2308, storage controller 2324, network controller 2306, sound controller 2320, and general purpose I/O interface 2312 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 24.

Figure 24:
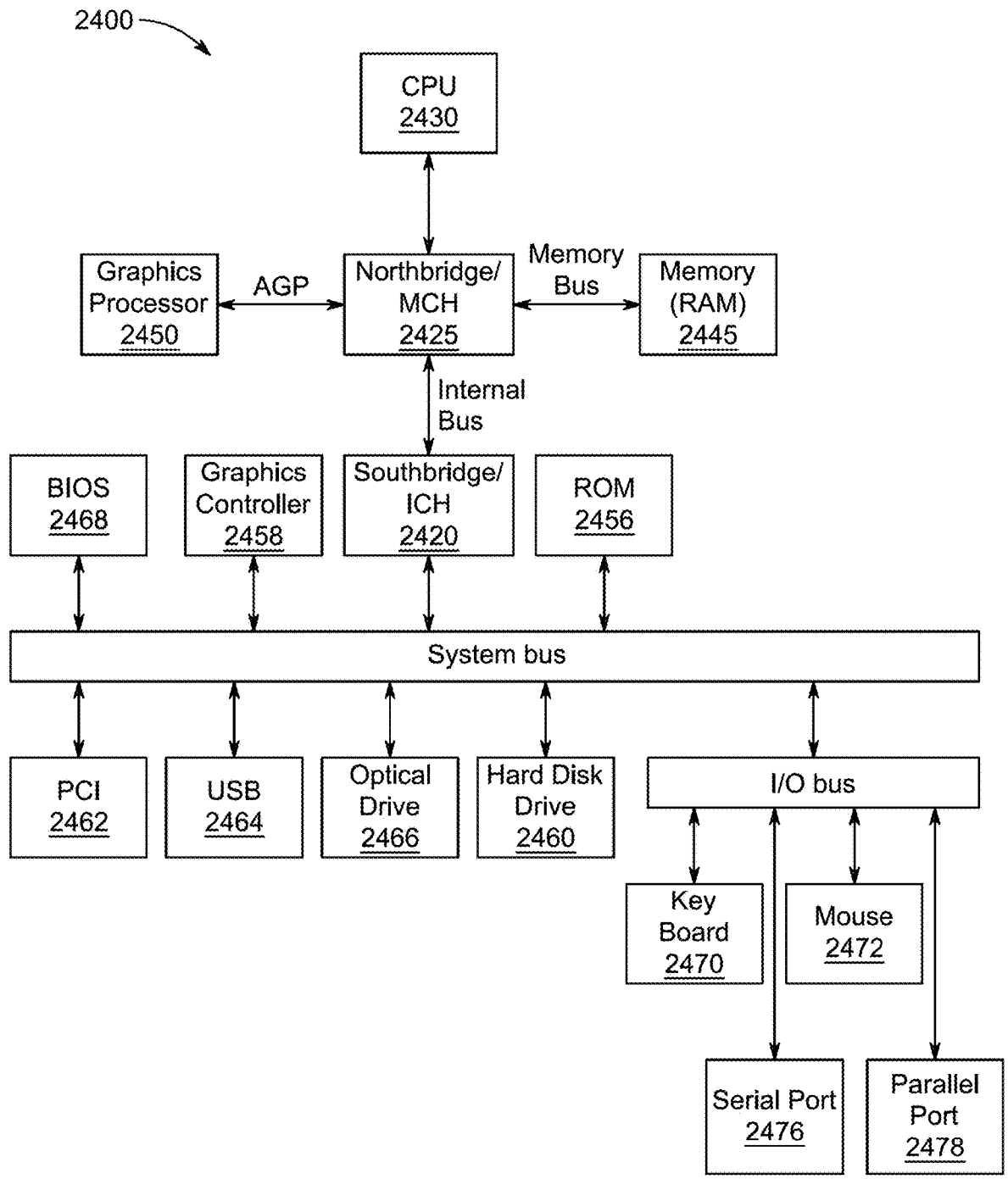
FIG. 24 is an exemplary schematic diagram of a data processing system used within the computing system, according to certain embodiments.

FIG. 24 shows a schematic diagram of a data processing system, according to certain embodiments, for performing the functions of the exemplary embodiments. The data processing system is an example of a computer in which code or instructions implementing the processes of the illustrative embodiments may be located.

In FIG. 24, data processing system 2400 employs a hub architecture including a north bridge and memory controller hub (NB/MCH) 2425 and a south bridge and input/output (I/O) controller hub (SB/ICH) 2420. The central processing unit (CPU) 2430 is connected to NB/MCH 2425. The NB/MCH 2425 also connects to the memory 2445 via a memory bus, and connects to the graphics processor 2450 via an accelerated graphics port (AGP). The NB/MCH 2425 also connects to the SB/ICH 2420 via an internal bus (e.g., a unified media interface or a direct media interface). The CPU Processing unit 2430 may contain one or more processors and even may be implemented using one or more heterogeneous processor systems.

Figure 25:
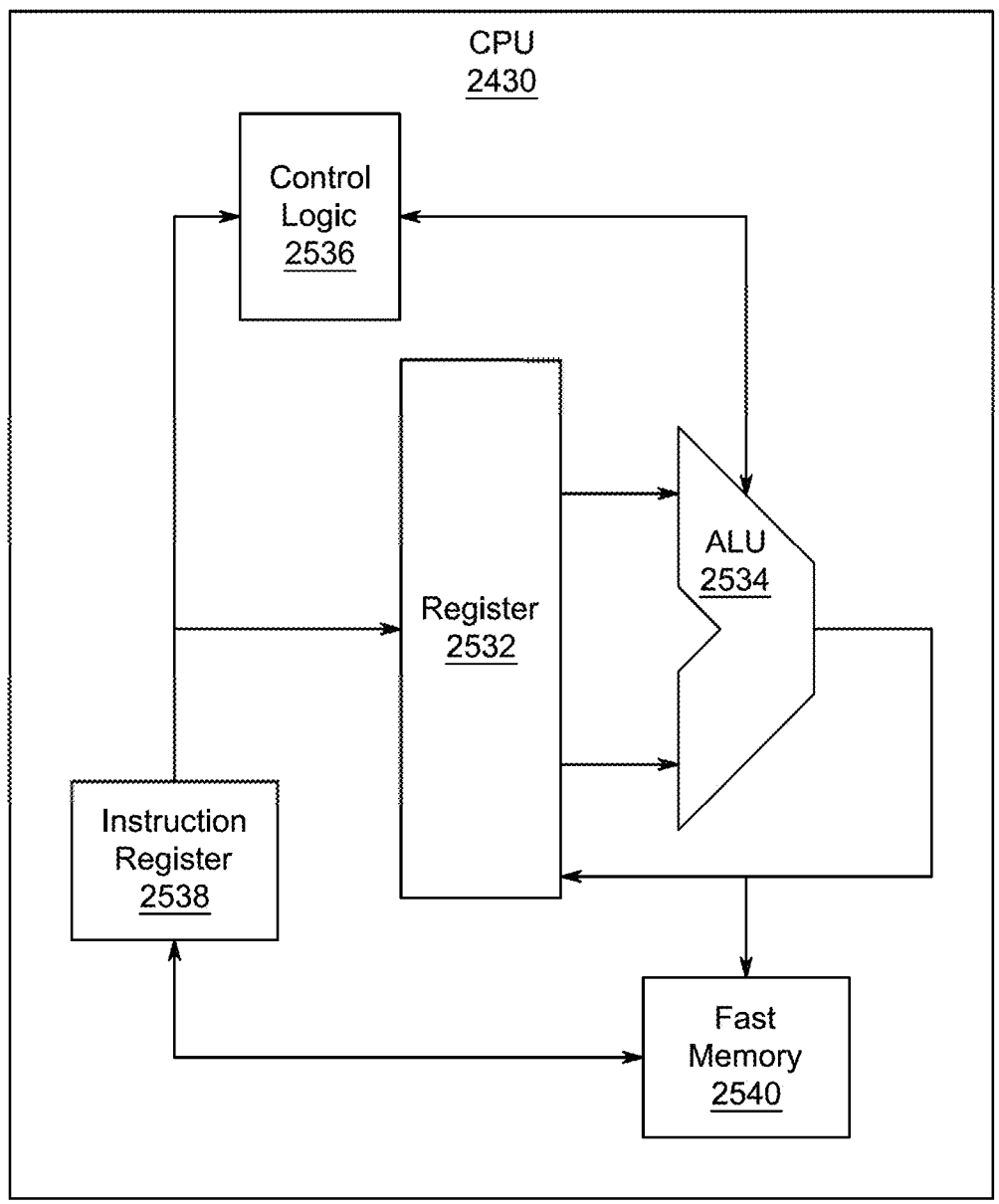
FIG. 25 is an exemplary schematic diagram of a processor used with the computing system, according to certain embodiments.

For example, FIG. 25 shows one implementation of CPU 2430. In one implementation, the instruction register 2538 retrieves instructions from the fast memory 2540. At least part of these instructions are fetched from the instruction register 2538 by the control logic 2536 and interpreted according to the instruction set architecture of the CPU 2430. Part of the instructions can also be directed to the register 2532. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 2534 that loads values from the register 2532 and performs logical and mathematical operations on the loaded values according to the instructions. The results from these operations can be feedback into the register and/or stored in the fast memory 2540. According to certain implementations, the instruction set architecture of the CPU 2430 can use a reduced instruction set architecture, a complex instruction set architecture, a vector processor architecture, a very large instruction word architecture. Furthermore, the CPU 2430 can be based on the Von Neuman model or the Harvard model. The CPU 2430 can be a digital signal processor, an FPGA, an ASIC, a PLA, a PLD, or a CPLD. Further, the CPU 2430 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 24, the data processing system 2400 can include that the SB/ICH 2420 is coupled through a system bus to an I/O Bus, a read only memory (ROM) 2456, universal serial bus (USB) port 2464, a flash binary input/output system (BIOS) 2468, and a graphics controller 2458. PCI/PCIe devices can also be coupled to SB/ICH 2488 through a PCI bus 2462.

The PCI devices may include, for example, Ethernet adapters, add-in cards, and PC cards for notebook computers. The Hard disk drive 2460 and CD-ROM 2466 can use, for example, an integrated drive electronics (IDE) or serial advanced technology attachment (SATA) interface. In one implementation the I/O bus can include a super I/O (SIO) device.

Further, the hard disk drive (HDD) 2460 and optical drive 2466 can also be coupled to the SB/ICH 2420 through a system bus. In one implementation, a keyboard 2470, a mouse 2472, a parallel port 2478, and a serial port 2476 can be connected to the system bus through the I/O bus. Other peripherals and devices that can be connected to the SB/ICH 2420 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 26:
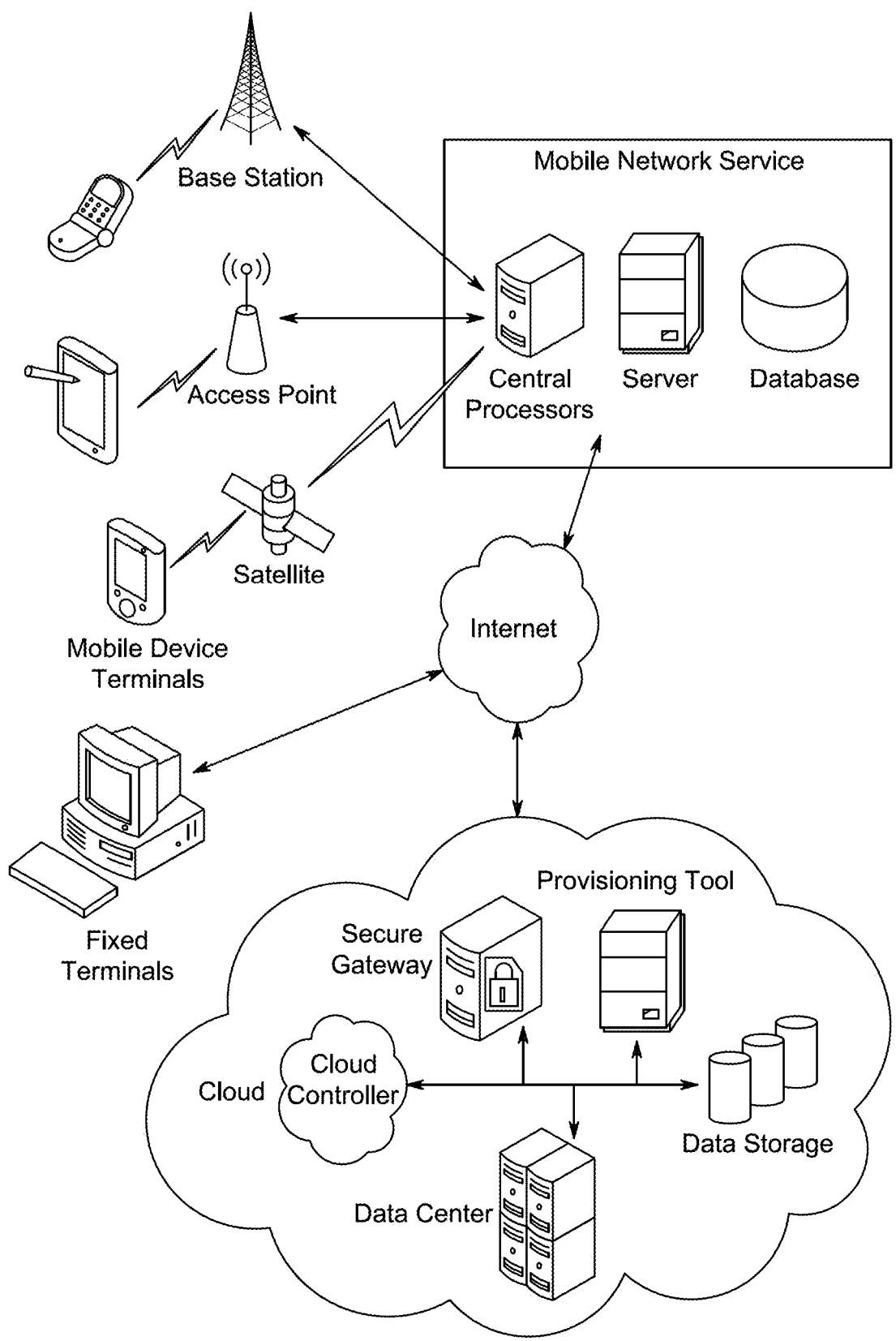
FIG. 26 is an illustration of a non-limiting example of distributed components which may share processing with the controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 26, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. A method of emulsion detection, the method comprising:
   obtaining a plurality of samples containing water and a matrix material from a formation with water percentage ranging from 0 vol. % to 100 vol. %;
   conducting an initial SIP measurement of the volume of the formation to determine an initial RCV of the matrix material; by
   obtaining the real-time SIP measurements of the volume of the formation using an SIP device that comprises:
   an SIP column including a plurality of potential electrodes arranged along a longitudinal direction of the SIP column; and two current electrodes positioned on opposing ends of the SIP column; Wherein
   an electrical current is injected into the formation through two current electrodes, propagating through the formation and encountering varying resistances; wherein
   these resistances influence the current flow, which is detected as potential changes by the potential electrodes;
   conducting a plurality of SIP measurements of the plurality of samples to determine a plurality of RCVs; and
   determining a first threshold value based on the plurality of RCVs: then
   executing an oil production process from a volume of the formation;
   while executing the oil production process, conducting real-time spectral induced polarization (SIP) measurements of the volume of the formation to determine a real-time real conductivity value (RCV) of the matrix material in the volume of the formation;
   while executing the oil production process, conducting real-time laser measurements of the volume of the formation to determine a real-time particle size value of the matrix material;
   determining an onset of water-in-oil (W/O) emulsion formation in the volume of the formation by analyzing the real-time RCV of the matrix material; and
   identifying the onset of the W/emulsion formation when the real-time RCV first exceeds the first threshold value; and
   confirming the onset of the W/O emulsion formation when the real-time particle size value exceeds a second threshold value; wherein
   the first threshold value is at least 100 times the initial RCV.

2. The method of claim 1, wherein:
the first threshold value is at least 1000 times the initial RCV.

3. The method of claim 1, wherein:
the onset of the W/O emulsion formation is identified when the real-time RCV first becomes at least 100 times of the initial RCV before reaching a maximum value and then decreasing.

4. The method of claim 1, further comprising:
conducting a plurality of laser measurements of the plurality of samples to determine a plurality of particle sizes; and
determining the second threshold value by comparing the plurality of RCVs and the plurality of particle sizes.

5. The method of claim 1, further comprising:
plotting the plurality of RCVs against the water percentage of the plurality of samples; and
determining a critical water concentration for the onset of the W/O emulsion formation.

6. The method of claim 5, further comprising:
determining a range of water percentage for the W/O emulsion formation.

7. The method of claim 1, wherein:
the initial SIP measurement and the real-time SIP measurements are performed at a frequency of 0.1 Hz or more, and 100 Hz or less.

8. The method of claim 1, wherein:
the initial SIP measurement and the real-time SIP measurements are performed at a single frequency or a plurality of individual frequencies.

9. The method of claim 8, wherein:
the initial SIP measurement and the real-time SIP measurements are performed at at least one frequency selected from the group consisting of 0.1 Hz, 1 Hz, 10 Hz or 100 Hz.

10. The method of claim 8, wherein:
the initial SIP measurement and the real-time SIP measurements do not include frequency sweeps over a frequency range.

11. A method of emulsion detection, comprising:
executing an oil production process from a volume of a formation: While
executing the oil production process, obtaining real-time spectral induced polarization (SIP) measurements of the volume of the formation to determine a real-time real conductivity value (RCV) of a matrix material in the volume of the formation;
determining an onset of water-in-oil (W/O) emulsion formation in the volume of the formation by analyzing the real-time RCV of the matrix material; and
identifying the onset of the W/G emulsion formation when the real-time RCV first exceeds a first threshold value;
obtaining the real-time SIP measurements of the volume of the formation using an SIP device that comprises:
an SIP column including a plurality of potential electrodes arranged along a longitudinal direction of the SIP column; and
two current electrodes positioned on opposing ends of the SIP column; Wherein
an electrical current is injected into the formation through two current electrodes, propagating through the formation and encountering varying resistances; wherein
these resistances influence the current flow, which is detected as potential changes by the potential electrodes.

12. The method of claim 11, wherein obtaining the SIP measurements comprises:
obtaining a first set of SIP measurements between two potential electrodes of the plurality of potential electrodes; and
obtaining a second set of SIP measurements between another two potential electrodes of the plurality of potential electrodes.

13. A method of emulsion detection, comprising:
executing an oil production process from a volume of a formation;
while executing the oil production process, obtaining; real-time Spectral induced polarization (SIP) measurements of the volume of the formation to determine a real-time real conductivity value (RCV) of a matrix material in the volume of the formation; by
placing potential electrodes and current electrodes adjacent to the volume of the formation; and
two current electrodes positioned on opposing ends of the SIP measurements of the volume of the formation; Wherein
an electrical current is injected into the volume of the formation through two current electrodes, propagating through the formation and encountering varying resistances; wherein
these resistances influence the current flow, which is detected as potential changes by the potential electrodes;
determining an onset of water-in-oil (W/o) emulsion formation in the volume of the formation by analyzing the real-time RCV of the matrix material; and identifying the onset of the W/G emulsion formation when the real-time RCV first exceeds a first threshold value; and measuring a set of data via the potential electrodes.

14. The method of claim 13, wherein:
the potential electrodes and the current electrodes are placed at intervals along a borehole adjacent to the volume of the formation or on a ground surface above the volume of the formation.

15. The method of claim 13, wherein:
injecting the alternating electrical current and measuring the set of data are executed simultaneously.

16. The method of claim 13, wherein:
the set of data include the real-time RCV and at least one selected from the group consisting of an imaginary conductivity, a phase shift and an impedance distribution.

* * * * *